US011760727B2

(12) United States Patent
Yang et al.

(10) Patent No.: US 11,760,727 B2
(45) Date of Patent: Sep. 19, 2023

(54) N-AROMATIC AMIDE COMPOUNDS, PREPARATION METHODS AND USES THEREOF

(71) Applicant: Shenzhen EDK Pharmaceutical Technology Co., Ltd., Guangdong (CN)

(72) Inventors: Guohong Yang, Liaoning (CN); Lijun Yu, Guangdong (CN); Junze He, Inner Mongolia (CN); Meijuan Duan, Beijing (CN)

(73) Assignee: Shenzhen EDK Pharmaceutical Technology Co., Ltd., Shenzhen (CN)

( * ) Notice: Subject to any disclaimer, the term of this patent is extended or adjusted under 35 U.S.C. 154(b) by 0 days.

(21) Appl. No.: 17/214,834

(22) Filed: Mar. 27, 2021

(65) Prior Publication Data

US 2021/0214311 A1 Jul. 15, 2021

Related U.S. Application Data

(63) Continuation of application No. PCT/CN2019/106287, filed on Sep. 17, 2019.

(30) Foreign Application Priority Data

Sep. 28, 2018 (CN) .......................... 201811138268.6

(51) Int. Cl.
*C07D 231/16* (2006.01)
*C07D 231/12* (2006.01)
*A61K 9/00* (2006.01)
*A61K 9/20* (2006.01)
*A61K 47/10* (2017.01)
*A61K 47/26* (2006.01)
*C07D 209/18* (2006.01)
*C07D 209/42* (2006.01)

(52) U.S. Cl.
CPC .......... *C07D 231/16* (2013.01); *A61K 9/0019* (2013.01); *A61K 9/2018* (2013.01); *A61K 9/2059* (2013.01); *A61K 47/10* (2013.01); *A61K 47/26* (2013.01); *C07D 209/18* (2013.01); *C07D 209/42* (2013.01); *C07D 231/12* (2013.01)

(58) Field of Classification Search
CPC ........................... C07D 231/12; C07D 231/16
See application file for complete search history.

(56) References Cited

FOREIGN PATENT DOCUMENTS

| CA | 1053231 | 4/1979 |
| CN | 104245675 | 12/2014 |
| CN | 107400088 | 11/2017 |
| JP | 51082269 | 7/1976 |
| WO | WO9603385 | 2/1996 |
| WO | WO2007038444 | 4/2007 |
| WO | WO2019081477 | 5/2019 |

OTHER PUBLICATIONS

Registry No. 1920169-25-0, entered in STN on May 29, 2016; retrieved from Chemical Catalog in Registry.*
Registry No. 2372912-05-3, entered in STN on Sep. 3, 2019; retrieved from Chemical Library in Registry.*
Registry No. 2373405-83-3, entered in STN on Sep. 4, 2019; retrieved from Chemical Library in Registry.*
Dong, et al. Medicinal Chemistry Research (2019) 28: 380-386.*
CN 107400088 A (Zhao, et al.) Nov. 28, 2017 (abstract) STN [database online]. retrieved on Apr. 29, 2022; Accession No. 2017:1905637.*

(Continued)

*Primary Examiner* — Shawquia Jackson
(74) *Attorney, Agent, or Firm* — RANKIN, HILL & CLARK LLP

(57) ABSTRACT

The present invention relates to N-aromatic amide compounds with formula (I) and/or (II) and preparation methods therefor, pharmaceutical compositions and pharmaceutical formulations containing the compounds with formula (I) and/or (II), and use of the compounds with formula (I) and/or (II) in preparing a medicament for the treatment of diseases related to androgens. The definitions of $R_1$, $R_2$, $R_3$, $R_4$, $R_5$, $R_6$, $W_1$, $W_2$, $W_3$, $W_4$ and $W_5$ in the formula are the same as those in the description. The compounds with the formula (I) and/or (II) are capable of binding to the androgen receptors and have activity for anti-androgen and degrading androgen receptor. The compounds can be used alone or as compositions for the treatment of various androgen-related diseases such as prostate cancer, prostate hyperplasia, breast cancer, bladder cancer, ovarian cancer and the like, and also for the treatment of acne, hirsutism, psilosis and other diseases.

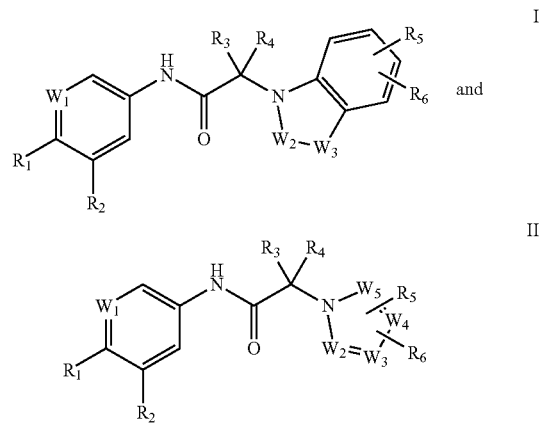

4 Claims, No Drawings

(56) References Cited

OTHER PUBLICATIONS

DE 2550566 A1(Moon, et al.) abstract retrieved from STN; Accession No. 1976:446670, May 20, 1976.*
WO 2019081477 A1 (Mueller, et al.) abstract retrieved from STN; Accession No. 2019:867640, May 2, 2019.*
RN1299363-11-3 STN 24.5, May 24, 2011. (Cited in International Search Report of PCT/CN2019/106287 dated Dec. 31, 2019).
RN1288359-74-9 STN 01.5, May 1, 2011. (Cited in International Search Report of PCT/CN2019/106287 dated Dec. 31, 2019).
RN1287181-00-3 STN 28.4, Apr. 28, 2011. (Cited in International Search Report of PCT/CN2019/106287 dated Dec. 31, 2019).
RN1387940-35-3 STN 08.8, Aug. 8, 2012. (Cited in International Search Report of PCT/CN2019/106287 dated Dec. 31, 2019).
Syo Ishida et al. Copper-Catalyzed Amination of Congested and Functionalized Angewandte Chemie, International Edition 15.8, pp. 11610-11614, 2017. (Cited in International Search Report of PCT/CN2019/106287 dated Dec. 31, 2019).
International Search Report of PCT/CN2019/106287 dated Dec. 31, 2019, 13 pages.
M. Iovu, C. Zalaru, F. Dumitrascu, C. Draghici, and E. Cristea. "New substituted 2-(pyrazol-l-yl) o-, m-, p-methylacetanilides with potential local anaesthetic and antiarrhythmic action—Part I." IL FARMACO, vol. 55, No. 5, pp. 362-368 (May 1, 2000). Cited in EESR.
C. Ferroni, A. Pepe, Y.S. Kim, S. Lee, A. Guerrini, M.D. Parenti, A. Tesei, A. Zamagni, M. Cortesi, N. Zaffaroni, M. De Cesare, G.L. Beretta, J.B. Trepel, S.V. Malhotra and G. Varchi. "1,4-Substituted Triazoles as Non-Steroidal Antiandrogens for Prostate Cancer Treatment." Journal of Medicinal Chemistry, vol. 60, No. 7, pp. 3082-3093 (Mar. 8, 2017). Cited in EESR.
W.S. Smith and R.Y. Moir. "1-Indoleacetic Acid." Canadian Journal of Chemistry, vol. 30, No. 5, pp. 411-421 (May 1, 1952). Cited in EESR.
Extended European Search Report of EP Serial No. 19866813.9 dated Apr. 12, 2022, 11 pages.
M. S. Sonopo et al., "Carbon-14 radiolabelling and tissue distribution evaluation of a potential anti-TB compound," Journal of Labeled Compounds and Radiopharmaceuticals, 2016, vol. 59, pp. 264-269.
R. Zhang et al., "Iron-Mediated Azidomethylation or Azidotrideuteromethylation of Active Alkenes with Azidotrimethylsilane and Dimethyl Sulfoxide," Advanced Synthesis & Catalysis, 2018, vol. 360, pp. 1384-1388.
RN1212085-33-0 (Cited in Japanese Office Action of JP 2021-542244 dated Jun. 7, 2022).
RN1212089-89-8 (Cited in Japanese Office Action of JP 2021-542244 dated Jun. 7, 2022).
RN1212104-60-3 (Cited in Japanese Office Action of JP 2021-542244 dated Jun. 7, 2022).
RN1212114-43-6 (Cited in Japanese Office Action of JP 2021-542244 dated Jun. 7, 2022).
RN1212122-17-2 (Cited in Japanese Office Action of JP 2021-542244 dated Jun. 7, 2022).
RN1212149-39-7 (Cited in Japanese Office Action of JP 2021-542244 dated Jun. 7, 2022).
RN1212197-09-5 (Cited in Japanese Office Action of JP 2021-542244 dated Jun. 7, 2022).
RN1212244-79-5 (Cited in Japanese Office Action of JP 2021-542244 dated Jun. 7, 2022).
RN1351679-21-4 (Cited in Japanese Office Action of JP 2021-542244 dated Jun. 7, 2022).
RN1351694-91-1 (Cited in Japanese Office Action of JP 2021-542244 dated Jun. 7, 2022).
RN1351698-66-2 (Cited in Japanese Office Action of JP 2021-542244 dated Jun. 7, 2022).
Japanese Office Action of JP 2021-542244 dated Jun. 7, 2022, 5 pages.
RN1387463-68-4 (Cited in Korean Office Action of 10-2021-7011156 dated Mar. 21, 2023).
RN1904465-33-3 (Cited in Korean Office Action of 10-2021-7011156 dated Mar. 21, 2023.
RN1909473-52-4 (Cited in Korean Office Action of 10-2021-7011156 dated Mar. 21, 2023.
RN1919396-36-3 (Cited in Korean Office Action of 10-2021-7011156 dated Mar. 21, 2023.
RN2184595-53-5 (Cited in Korean Office Action of 10-2021-7011156 dated Mar. 21, 2023.
RN2185323-84-4 (Cited in Korean Office Action of 10-2021-7011156 dated Mar. 21, 2023.
RN2197047-91-7 (Cited in Korean Office Action of 10-2021-7011156 dated Mar. 21, 2023.
Korean Office Action of KR 10-2021-7011156 dated Mar. 21, 2023.

* cited by examiner

N-AROMATIC AMIDE COMPOUNDS, PREPARATION METHODS AND USES THEREOF

TECHNICAL FIELD

The present invention relates to an N-aromatic amide compound, having effects of anti-androgen and degrading androgen receptors, a preparation method thereof, and a pharmaceutical use thereof. The compound can be used for treating diseases related to androgens such as prostate cancer, prostate hyperplasia, breast cancer, bladder cancer, acne, hirsutism, psilosis or the like.

BACKGROUND

Androgen receptors, which belong to the nuclear receptor family, are receptors for ligand-induced nuclear transcription factors. The androgen receptors, as an important cellular regulatory protein, play an important role in a series of physiological processes through endogenous androgens, including the development and maintenance of male secondary sexual characteristics, including muscle and bone mass, male hair, prostate growth, sperm development, and the like. Endogenous steroid androgens, known as male sex hormones, include testosterone and dihydrotestosterone (DHT). Testosterone is found as the major steroid androgen in the male serum and is produced mainly by the testis. In many peripheral tissues, such as the prostate and the skin, testosterone can be converted by 5α-reductase into dihydrotestosterone (DHT) which is an androgen with an enhanced activity.

Many diseases are linked to the level of androgens. As men get older, the level of androgens in vivo gradually decreases, along with muscle loss, osteoporosis and declined sexual function. By contrast, high level of androgens in vivo can also lead to some diseases, such as prostate cancer, prostate hyperplasia, acne, hirsutism, psilosis, and other androgen-related diseases.

Because prostate cancer is hormone-dependent, endocrine therapy for prostate cancer has been used as the longest, most mature, and most effective means. As early as 1941, Huggins and Hodges discovered surgical castration, for example, to remove testosterone source by removing both testes through surgical operation, and that estrogen can retard the progress of metastatic prostate cancer, and demonstrated the response of prostate cancer to androgen deprivation for the first time. However, clinical studies have shown that simple removal of the testes can lower the level of androgens in the blood, but cannot significantly lower the level of androgens in the prostate tissue, which is because there is an enzyme system in the prostate tissue that synthesizes androgens using steroids secreted by the adrenal gland as raw materials, and can convert the androgen (testosterone) into the more active androgen (dihydrotestosterone). Therefore, even if castration therapy is adopted, therapy for prostate cancer with anti-androgen drugs is also necessary.

In current, it is a standard therapy for treating prostate cancer to use anti-androgen drugs (androgen antagonists) to competitively block the binding of androgens to androgen receptors on prostate cells. Commonly used non-steroidal androgen receptor antagonists are shown as follows:

1. Flutamide is a first generation of non-steroidal androgen receptor antagonists (Endocrinology 1972, 91, 427-437; Biochemical Society Transactions 1979, 7, 565-569; Journal of Steroid Biochemistry 1975, 6, 815-819). The metabolite of flutamide, i.e., 2-hydroxyflutamide, as the main active form of flutamide, is capable of binding to the androgen receptors in the target tissue, blocking dihydrotestosterone from binding to the androgen receptors, and preventing the target tissue from uptaking the testosterone, thereby functioning as an antiandrogen. Due to large dosage, long term administration of flutamide may lead to gynecomastia, along with tumour and tenderness, as well as nausea, vomiting, diarrhea, occasional cutaneous reaction, denatured hemoglobin anemia, leukocytopenia and thrombocytopenia. In addition, during the treatment, flutamide may lead to antiandrogen withdrawal syndrome, and hepatotoxicity in few cases, and the like.

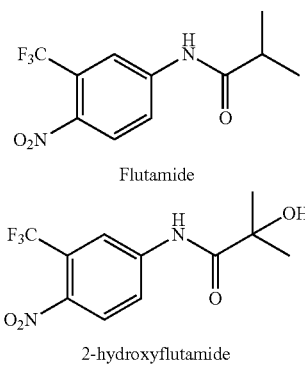

2. Bicalutumide is a second generation of non-steroidal androgen receptor antagonists (The Journal of Endocrinology 1987, 113, R7-R9; Urologic Clinics of North America 1991, 18, 99-110). This drug is a racemic isomer and the active ingredient thereof is the levoisomer. In addition to its anti-androgenic effect, bicalutumide is more effective than flutamide, with side effects reduced by 70%. Similar to flutamide, bicalutumide is capable of binding to the androgen receptors in the target tissue, blocking dihydrotestosterone from binding to the androgen receptors, and preventing the target tissue from uptaking the testosterone, thereby functioning as an antiandrogen. The disadvantage of bicalutumide is that after a certain median duration (typically 18 to 24 months), almost all patients eventually develop hormone refractory prostate cancer. In addition, during the treatment, bicalutumide may also lead to antiandrogen withdrawal syndrome and the like.

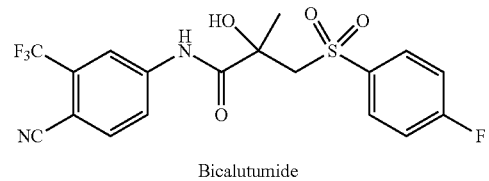 [SMILES: CC(O)(CS(=O)(=O)c1ccc(F)cc1)C(=O)Nc1ccc(C#N)c(C(F)(F)F)c1]

3. Enzalutamide (trade name: Xtandi) is a third generation of non-steroidal androgen receptor antagonists (Archives of Pharmacal Research 2015, 38 (11): 2076-82), which was approved by the FDA in 2012. It has a stronger androgen receptor antagonism, which acts as a new drug to endocrine therapy. The disadvantage is that it is expensive and can also develop hormone refractory prostate cancer. In addition, during the treatment, enzalutamide may cause patient to convulse. Therefore, the application of enzalutamide has been limited.

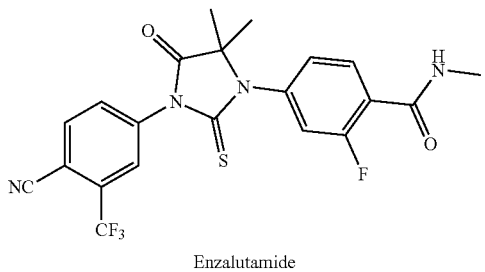 [SMILES: CNC(=O)c1ccc(N2C(=S)N(c3ccc(C#N)c(C(F)(F)F)c3)C(=O)C2(C)C)cc1F]

Enzalutamide

Hence, development of novel anti-androgen drugs, that are safer and more effective than exist drugs, has an important value and status in the treatment of androgen-related diseases, such as prostate cancer, prostate hyperplasia, breast cancer, bladder cancer, ovarian cancer and other diseases.

In the studies of the anti-androgen drugs, the inventor found an N-aromatic amide compound which has the effects of anti-androgen and degrading the androgen receptor, is safer and more effective than exist drugs, thereby the present invention is provided.

SUMMARY

An object of the present invention is to provide a new N-aromatic amide compound or a pharmaceutically acceptable salt thereof (hereinafter also referred as compound of the present invention), having anti-androgen activity and effect of degrading androgen receptors, which is safer and more effective than existing drugs and can be used for the prevention or treatment of androgen-related diseases, such as prostate cancer, prostate hyperplasia, breast cancer, bladder cancer, ovarian cancer, acne, hirsutism, psilosis, and the like. The N-aromatic amide compound has the following chemical structural formula (I) and/or (II):

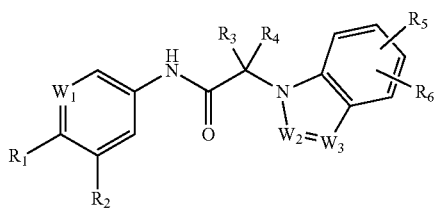

I

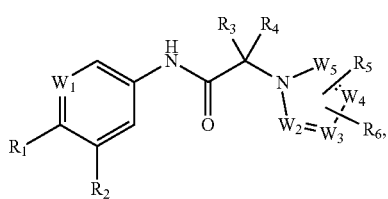

II wherein each of $R_1$ and $R_2$ is hydrogen atom, cyano group, nitro group, trifluoromethyl group or halogen; each of $R_3$ and $R_4$ is hydrogen atom, or $C_1$-$C_6$ alkyl group, or $R_3$ and $R_4$ together with carbon atom through which $R_3$ and $R_4$ are bound constitute a 3-6 membered cycloalkyl group; each of $R_5$ and $R_6$ is hydrogen atom, halogen, trifluoromethyl group, cyano group, nitro group, acetyl group,

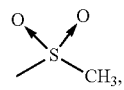

N-methylcarbamoyl group

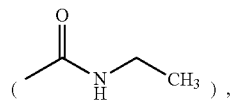, $C_1$-$C_6$ alkyl group, aryl group or substituted aryl group;

each of $W_1$, $W_2$, $W_3$, $W_4$ and $W_5$ is carbon atom or nitrogen atom, and in the formula (I), the chemical bond between $W_2$ and $W_3$ is a single bond or a double bond, and each of $R_5$ and $R_6$ is bound to any bondable site of the benzene ring of the group

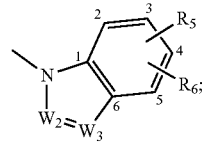

such as site 2, site 3, site 4, or site 5 as shown below,

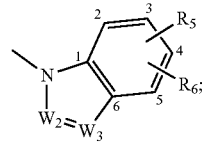

in the formula (II), the chemical bond between $W_2$ and $W_3$ is a double bond, the chemical bond between $W_4$ and $W_5$ is a double bond, and each of $R_5$ and $R_6$ is bound to any bondable site of the group

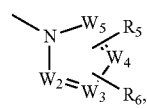

such as site 2, site 3, site 4, or site 5 as shown below,

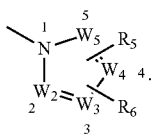

In a preferred embodiment, the N-aromatic amide compound with the formula (I) has the following chemical structural formula (III):

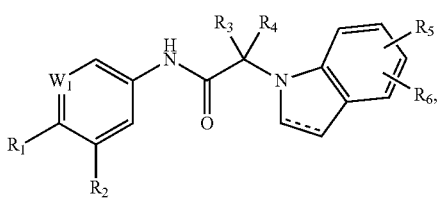

wherein each of $R_1$ and $R_2$ is hydrogen atom, cyano group, nitro group, trifluoromethyl group or halogen; each of $R_3$ and $R_4$ is hydrogen atom, or $C_1$-$C_6$ alkyl group, or $R_3$ and $R_4$ together with carbon atom through which $R_3$ and $R_4$ are bound constitute a 3-6 membered cycloalkyl group; each of $R_5$ and $R_6$ is hydrogen atom, halogen, trifluoromethyl group, cyano group, nitro group, acetyl group,

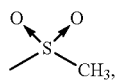

N-methylcarbamoyl group

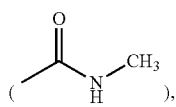

$C_1$-$C_6$ alkyl group, aryl group or substituted aryl group; $W_1$ is carbon atom or nitrogen atom; $W_2$ and $W_3$ are carbon atom, and each of $R_5$ and $R_6$ is bound to any bondable site of the benzene ring of the group

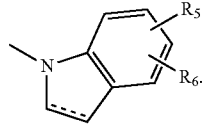

In another preferred embodiment, the N-aromatic amide compound with the formula (II) has the following chemical structural formula (IV):

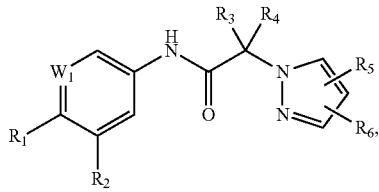

wherein each of $R_1$ and $R_2$ is hydrogen atom, cyano group, nitro group, trifluoromethyl group or halogen; each of $R_3$ and $R_4$ is hydrogen atom, or $C_1$-$C_6$ alkyl group, or $R_3$ and $R_4$ together with carbon atom through which $R_3$ and $R_4$ are bound constitute a 3-6 membered cycloalkyl group; each of $R_5$ and $R_6$ is hydrogen atom, halogen, trifluoromethyl group, cyano group, nitro group, acetyl group,

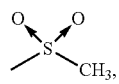

N-methylcarbamoyl group

$C_1$-$C_6$ alkyl group, aryl group or substituted aryl group; $W_1$ is carbon atom or nitrogen atom; $W_2$ is nitrogen atom; $W_3$, $W_4$ and $W_5$ are carbon atom; and each of $R_5$ and $R_6$ is bound to any bondable site of the group

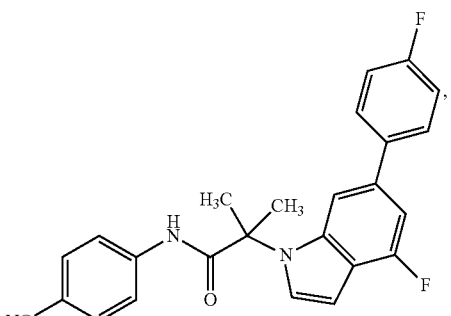

In the case where the above formulas (I), (II), (III) and (IV) includes chiral atom in their molecules, their stereo configurations may be racemic, levorotatory (R-configuration) and/or dextrorotatory (S-configuration). Hence, that present invention also include stereoisomers of the N-aromatic amide compound with the formula (I) and/or (II) or the pharmaceutically acceptable salt thereof, i.e., their levorotatory, dextrorotatory and/or racemic isomer.

In another preferred embodiment, the compound with the formula (I), (II) is selected from the group consisting of:

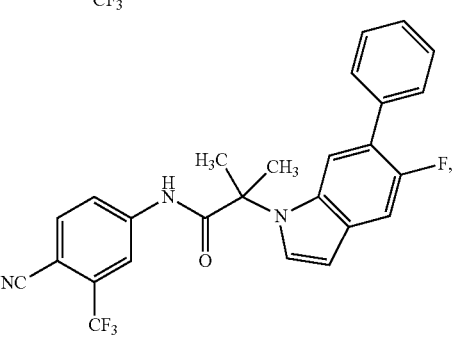

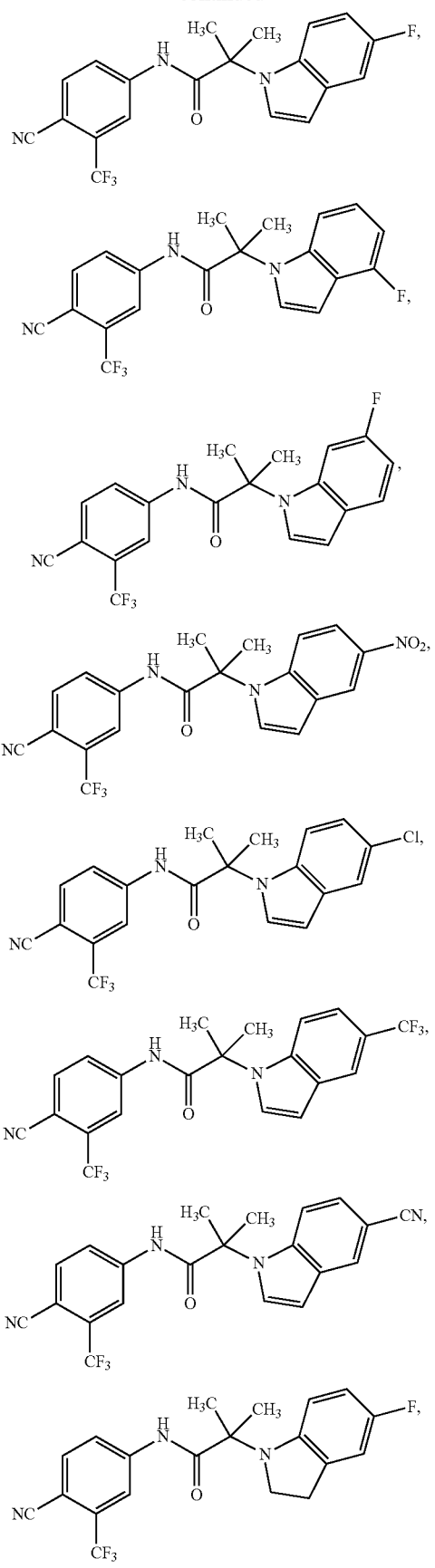
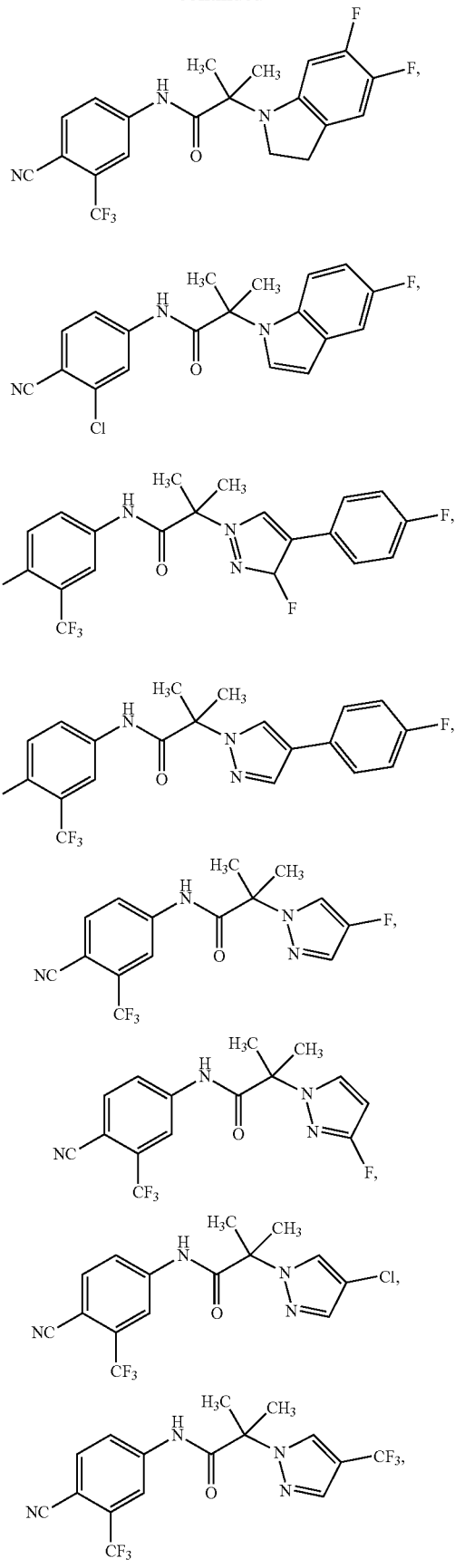

-continued
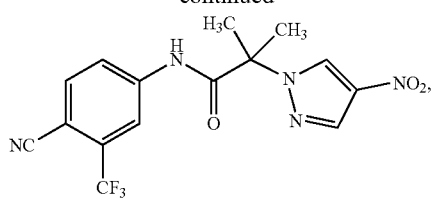
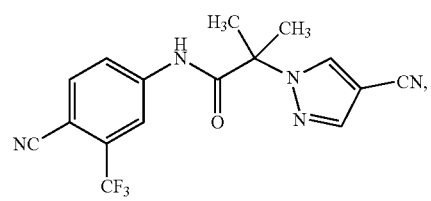
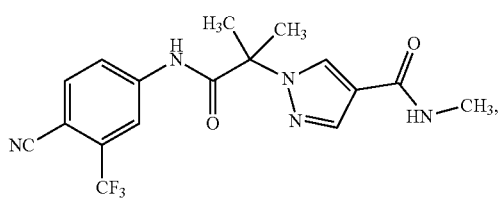
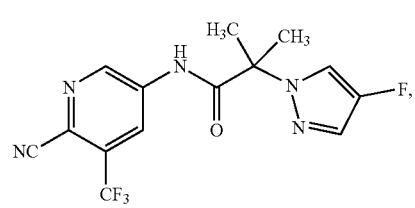
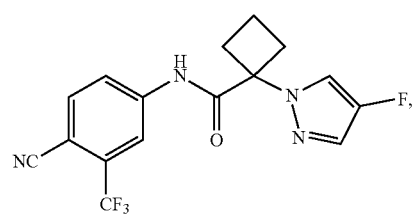
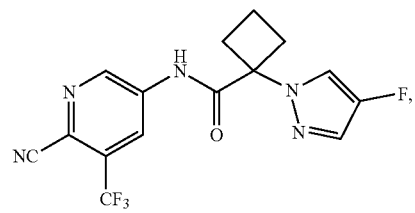
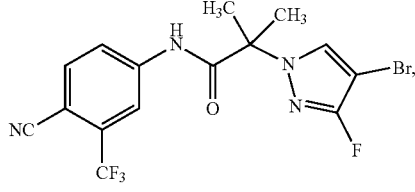
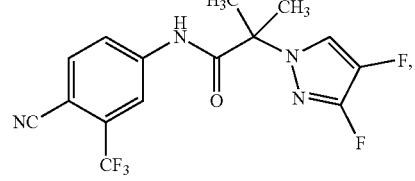
-continued
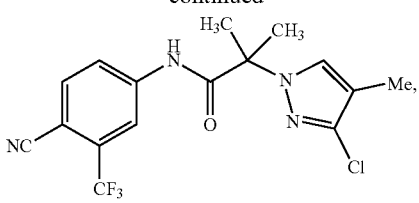
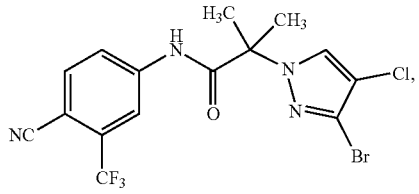
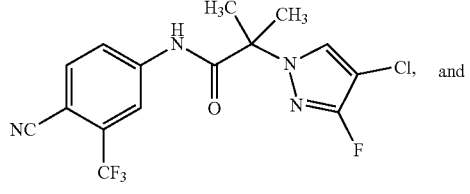
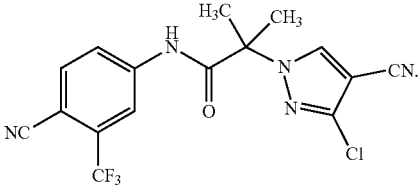
The present invention also includes active metabolites, such as in vivo primary and/or secondary metabolites, of the N-aromatic amide compound with the formula (I) and/or (II) or the pharmaceutically acceptable salt thereof or the stereoisomer thereof.
For example, the in vivo primary metabolite may be:
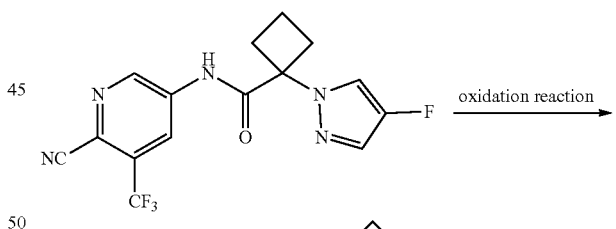
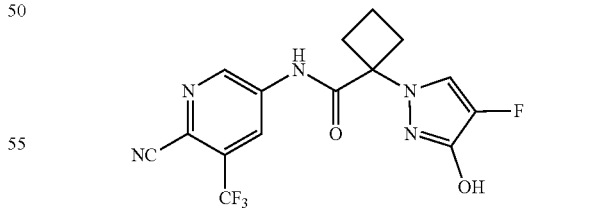
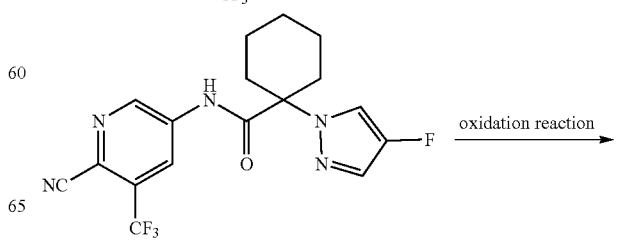

-continued
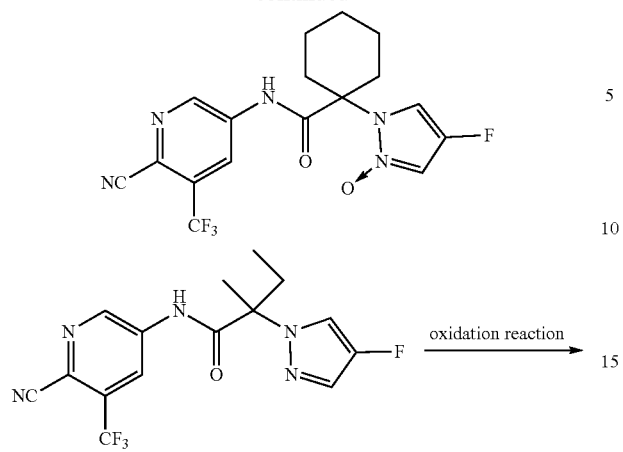
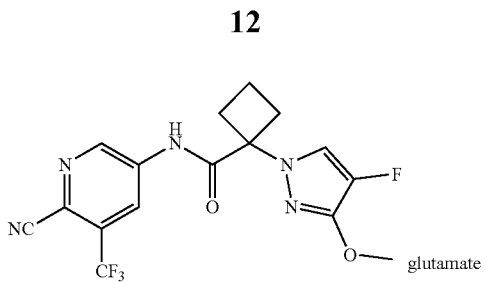
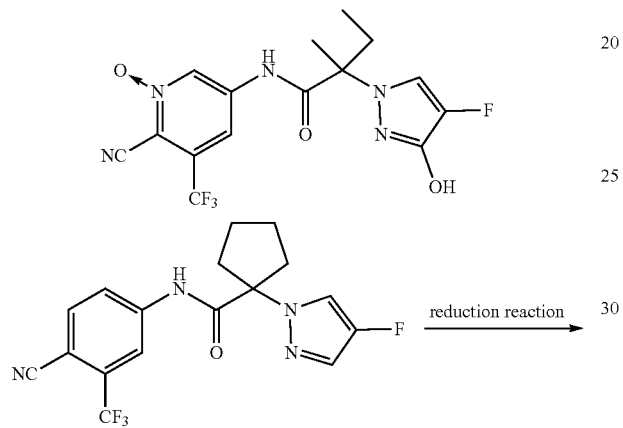
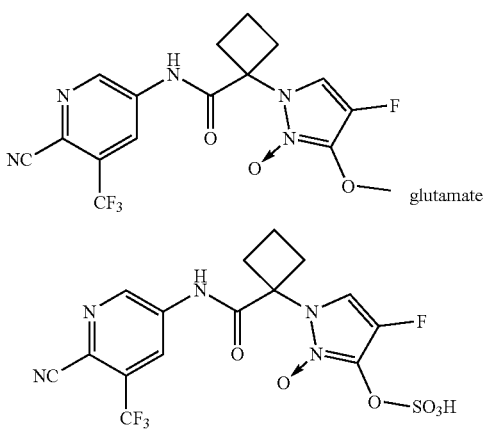
For example, the in vivo secondary metabolite may be:
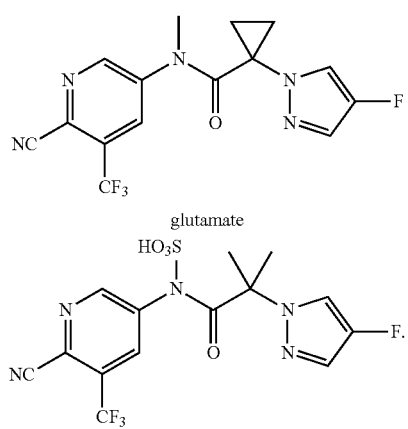
For example, the in vivo primary and secondary metabolites may be:
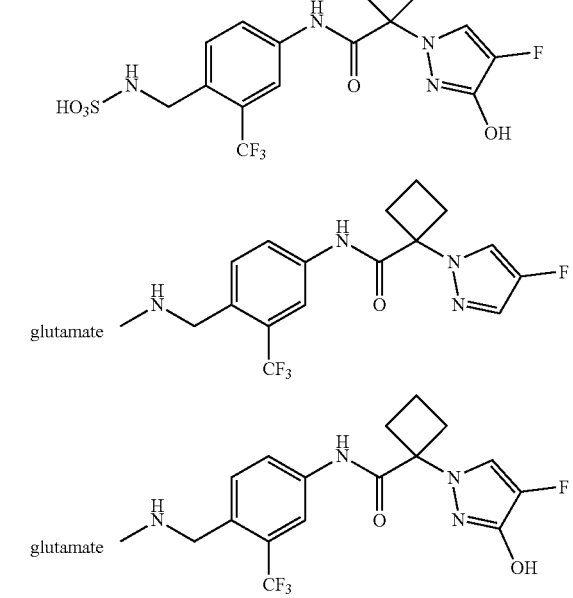

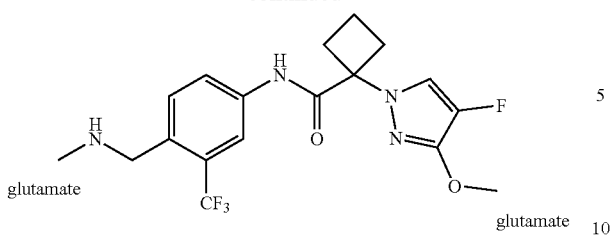

glutamate glutamate

The N-aromatic amide compounds with the formula (I) and/or (II) of the present invention may also be present in the form of solvates such as hydrates, and thus, the present invention also includes the solvates, such as hydrates, of the N-aromatic amide compound with the formula (I) and/or (II) or the pharmaceutically acceptable salt thereof or the stereoisomer thereof.

In addition, the N-aromatic amide compounds with the formula (I) and/or (II) of the present invention may also be present in the form of prodrugs which can be converted in vivo into the N-aromatic amide compound with the formula (I) and/or (II). Hence, the present invention also includes the prodrugs of the N-aromatic amide compound with the formula (I) and/or (II) or the pharmaceutically acceptable salt thereof or the stereoisomer thereof.

$R_8$ = hydrogen atom, cyano, nitro, trifluoromethyl, halogen, or the other groups Another object of the present invention is to provide a preparation method for the N-aromatic amide compound with the formula (I), as shown in the following chemical equation, the method comprises steps of:
1) reacting compound (V) and compound (VI) (both of them are commercially available) to obtain compound (VII);
2) reacting the compound (VII) and compound (VIII) (which can be directly commercially obtained, or synthesized by the method of Pure Appl. Chem. 1991 63 (3): 419-422, Chemical Reviews, 1979 95 (7): 2457-2483, and Journal of Organometallic Chemistry. 1999 576: 147-168) in the presence of a catalyst, a ligand and a base to produce the target compound with the structural formula (I);

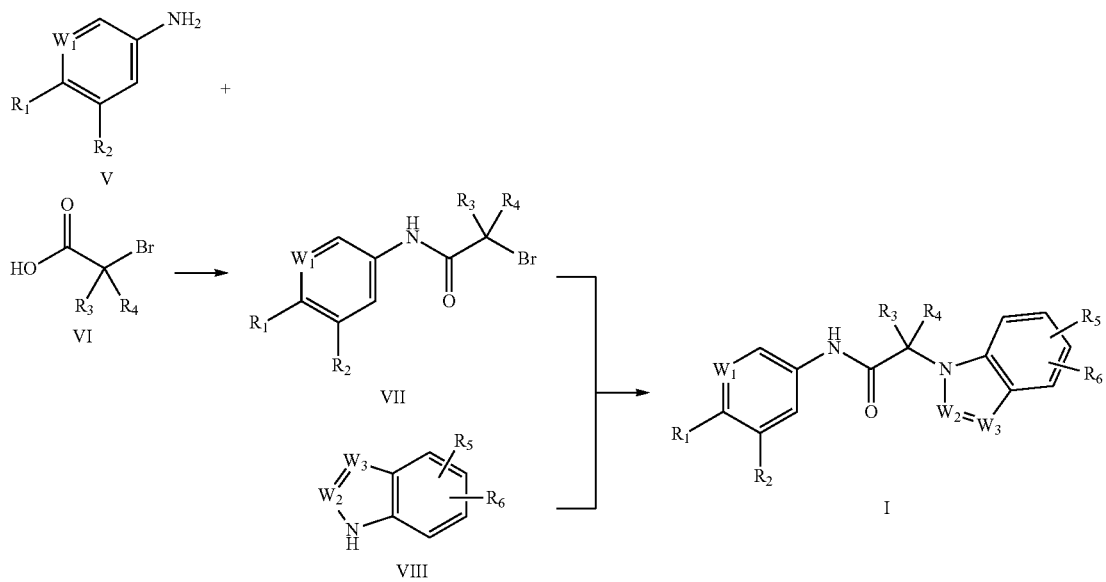

For example, the prodrug may be:

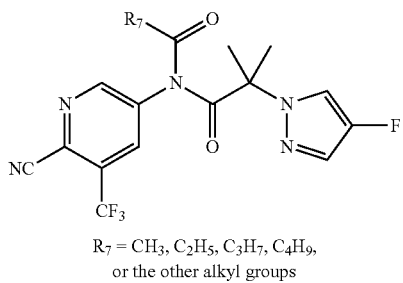

$R_7$ = $CH_3$, $C_2H_5$, $C_3H_7$, $C_4H_9$, or the other alkyl groups wherein the compound VIII may be, in some cases, directly commercially obtained or, in some cases, synthesized according to the scheme described below. For example, a corresponding compound (XII) may be synthesized.

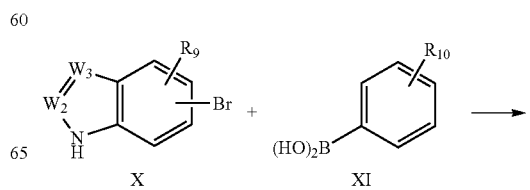

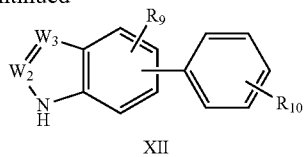

XII wherein the definitions of $R_1$, $R_2$, $R_3$, $R_4$, $R_5$, $R_6$, $W_1$, $W_2$ and $W_3$ shown in the chemical equation are the same as those of $R_1$, $R_2$, $R_3$, $R_4$, $R_5$, $R_6$, $W_1$, $W_2$ and $W_3$ in the N-aromatic amide compounds with the formula (I) of the present invention as described above, respectively; each of $R_9$ and $R_{10}$ is a hydrogen atom, halogen, trifluoromethyl group, cyano group, nitro group, acetyl group, clohexyl phosphine, and the base is a strong base selected from sodium hydroxide and potassium hydroxide.

Another object of the present invention is to provide a preparation method for the N-aromatic amide compound with the formula (II), as shown in the following chemical equation. The method comprises the steps of:

1) reacting compound (V) and compound (VI) (both of them are commercially available) to obtain compound (VII);

2) reacting the compound (VII) and compound (IX) (which can be directly commercially obtained, or synthesized by the method of Pure Appl. Chem. 1991 63 (3): 419-422, Chemical Reviews. 1979 95 (7): 2457-2483, and Journal of Organometallic Chemistry. 1999 576: 147-168) in the presence of a catalyst, a ligand and a base to produce the target compound with the structural formula (II);

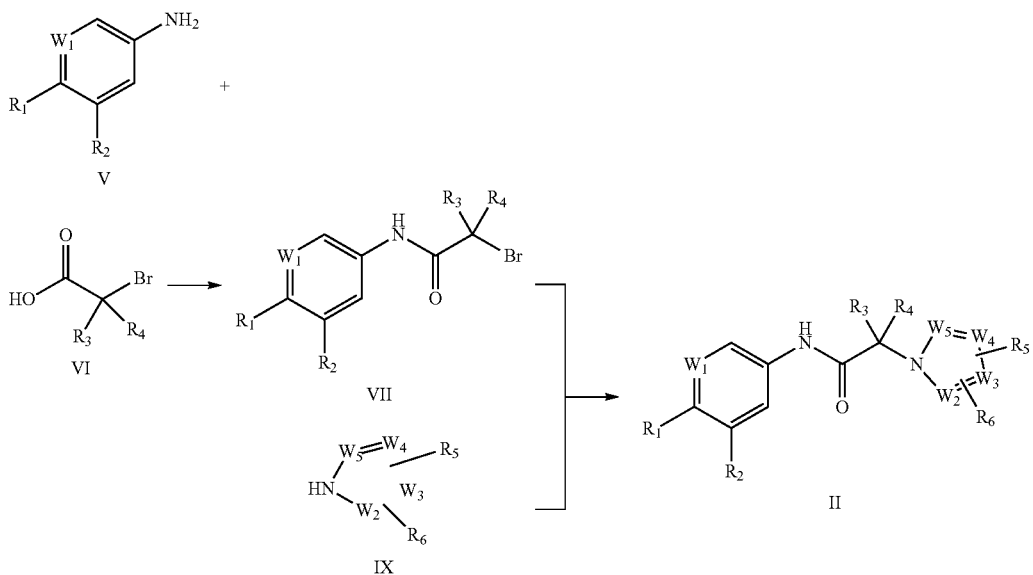

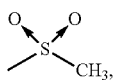

N-methylcarbamoyl group

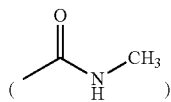

or $C_1$-$C_6$ alkyl group.

In one embodiment, the catalyst is copper(I) bromide-dimethyl sulfide, the ligand is triphenyl phosphine or tricyclohexyl phosphine, and the base is a weak base selected from the group consisting of sodium carbonate, sodium bicarbonate, potassium carbonate, potassium bicarbonate, trisodium phosphate, sodium dihydrogen phosphate, disodium hydrogen phosphate, tripotassium phosphate, potassium dihydrogen phosphate and dipotassium hydrogen phosphate.

In another embodiment, the catalyst is copper(I) bromide-dimethyl sulfide, the ligand is triphenyl phosphine or tricywherein the compound IX may be, in some cases, directly commercially obtained or, in some cases, synthesized according to the scheme described below. For example, a corresponding compound (XV) may be synthesized.

wherein the definitions of $R_1$, $R_2$, $R_3$, $R_4$, $R_5$, $R_6$, $W_1$, $W_2$, $W_3$, $W_4$ and $W_5$ shown in the chemical equation are the same as those of $R_1$, $R_2$, $R_3$, $R_4$, $R_5$, $R_6$, $W_1$, $W_2$, $W_3$, $W_4$ and $W_5$ in the N-aromatic amide compounds with the formula (II) of the present invention as described above, respectively;

each of $R_{11}$ and $R_{12}$ is a hydrogen atom, halogen, trifluoromethyl group, cyano group, nitro group, acetyl group,

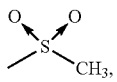

N-methylcarbamoyl group

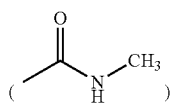

or $C_1$-$C_6$ alkyl group.

In one embodiment, the catalyst is copper(I) bromide-dimethyl sulfide, the ligand is triphenyl phosphine or tricyclohexyl phosphine, and the base is a weak base selected from the group consisting of sodium carbonate, sodium bicarbonate, potassium carbonate, potassium bicarbonate, trisodium phosphate, sodium dihydrogen phosphate, disodium hydrogen phosphate, tripotassium phosphate, potassium dihydrogen phosphate and dipotassium hydrogen phosphate.

In another embodiment, the catalyst is copper(I) bromide-dimethyl sulfide, the ligand is triphenyl phosphine or tricyclohexyl phosphine, and the base is a strong base selected from sodium hydroxide and potassium hydroxide.

A further object of the present invention is to provide a use of the N-aromatic amide compound with the formula (I) and/or (II) or the pharmaceutically acceptable salt thereof in preparing a medicament for the prevention or treatment of diseases related to androgens.

An another object of the present invention is to provide a method for treating or preventing diseases related to androgens, comprising administering the therapeutically or prophylactically effective amount of the N-aromatic amide compound with the formula (I) and/or (II) or the pharmaceutically acceptable salt thereof to a mammal in need.

In the present application, the androgen-related diseases include, but are not limited to, prostate cancer, prostate hyperplasia, breast cancer, bladder cancer, ovarian cancer, acne, hirsutism, and psilosis.

In the present application, the term "aryl group" refers to 5- to 10-membered aromatic monocyclic or bicyclic carbocyclic ring groups or monocyclic or bicyclic heterocyclic groups containing heteroatoms selected from N, O and S, which are unsubstituted or substituted with substituents, wherein one of the bicyclic ring may be hydrogenated, including, for example, phenyl, naphthyl, dihydronaphthyl, tetrahydronaphthyl, pyridyl, pyridazinyl, pyrimidinyl, pyrazinyl, furanyl, imidazolyl, pyranyl, pyrazolyl, oxazolyl, isoxazolyl, thiazolyl, isothiazolyl, thiophenyl, purinyl, benzofuranyl, benzothiophenyl, diazinyl, isobenzothiophenyl, isobenzofuranyl, indolyl, isoindolyl, quinolyl, isoquinolyl, and the like. The substituents are selected from the group consisting of hydrogen atom, alkyl group, halogen, trifluoromethyl group, cyano group, nitro group and the like.

In the present application, the term "substituted aryl group" refers to an aryl group substituted with one, two, three or more substituents selected from the group consisting of alkyl group, halogen, trifluoromethyl group, cyano group, nitro group and the like.

The term "alkyl group" herein, as a group or part of a group, refers to a straight or branched saturated hydrocarbon group. The examples of "alkyl group" include methyl, ethyl, n-propyl, isopropyl, n-butyl, isobutyl, sec-butyl, tertiary butyl, n-amyl, isoamyl, neoamyl or hexyl or the like, preferably, the alkyl group contains 1 to 6 carbon atoms, which can be represented as $C_1$-$C_6$ alkyl group, and more preferably, the alkyl group contains 1 to 4 carbon atoms, which can be represented as $C_1$-$C_4$ alkyl group.

In the present application, the term "3-6 membered cycloalkyl group" refers to a monocyclic or bicyclic carbocyclic ring having 3 to 6 carbon atoms, including, but not limited to, cyclopropyl, cyclobutyl, cyclopentyl and cyclohexyl.

In the present application, the term "halogen" refers to fluorine, chlorine, bromine or iodine.

In the present application, the term "copper(I) bromide-dimethyl sulfide" refers to $CuBr·S(Me)_2$.

In the present application, ⁓ represents that the chemical bond between two terminal atoms (in the compounds of the invention, the terminal atom is a carbon atom or a nitrogen atom) is a single bond or a double bond.

In the present application, the term "mammal" includes, but is not limited to, primate (such as ape and human), equine (including horse), canidae (such as dog), felidae, domestic livestock (such as hoofed animals, like pig, goat, sheep, etc.), as well as domestic pet and zoo animal. Preferably, the mammal is a human.

In the present application, the "pharmaceutically acceptable salt" refers to a salt formed by the reaction between a pharmaceutical non-toxic acid and the basic portion of the N-aromatic amide compound with formula (I) and/or (II) of the present invention, including, for example, hydrochloride, acetate, hydrobromide, sulfate, bisulfate, carbonate, bicarbonate, sulfite, phosphate, hydrogen phosphate, oxalate, malonate, valerate, borate, p-toluenesulfonate, mesylate, tartrate, benzoate, lactate, citrate, maleate, fumarate, malate, salicylate, mandelate, succinate, gluconate, lactobionate, etc., which can be prepared by methods well known to those skilled in the art.

It has been experimentally demonstrated that the N-aromatic amide compounds with the formula (I) and/or (II) of the present invention are capable of binding to the androgen receptor, and have significant activity for anti-androgen and degrading androgen receptor. The compounds can be used alone or as compositions for the prevention or treatment of various androgen-related diseases including, for example, prostate cancer, prostate hyperplasia, breast cancer, bladder cancer, ovarian cancer, and also for the prevention or treatment of acne, hirsutism, psilosis and other disease.

Hence, the present invention also provides a pharmaceutical composition comprising the N-aromatic amide compound with the formula (I) and/or (II) or the pharmaceutically acceptable salt thereof, and a pharmaceutical formulation comprising the N-aromatic amide compound with the formula (I) and/or (II) or the pharmaceutically acceptable salt thereof and pharmaceutically acceptable carriers.

The pharmaceutically acceptable carrier may include a conventional pharmaceutical carrier in the art, such as diluent, filler, binder, disintegrant, lubricant, dissolvant, solubilizer, and the like, including, but not limited to, starch, pregelatinized starch, carboxymethyl starch sodium, powdered sugar, lactose, calcium phosphate, magnesium stearate, talc, Aerosil, dextrin, cellulose and derivatives thereof (such as hydroxyethyl cellulose, hydroxypropyl cellulose, hydroxypropyl methylcellulose (HPMC) and the like), microcrystalline cellulose, mannitol, polysorbate 80, polyethylene glycol, water, injection water, physiological saline, glucose solution and the like.

The pharmaceutical compositions and pharmaceutical formulations of the present invention may also include various other common additives, such as preservative, emulsifier, suspending agent, flavoring agent, and the like.

The pharmaceutical compositions of the present invention may be prepared into any suitable dosage form that is pharmaceutically acceptable, including, but not limited to, for example, tablets, capsules, pills, granules, syrups, injections, solutions, suspensions, and the like.

The N-aromatic amide compound with the formula (I) and/or (II) or the pharmaceutically acceptable salt thereof of the present invention may be administered to mammals (such as humans) by any effective route. The route includes oral, intravenous, intraperitoneal, intramuscular, topical, transdermal, transocular, transnasal, inhalation, subcutaneous, intramuscular, oral, sublingual, rectal route or the like. The N-aromatic amide compound with the formula (I) and/or (II) or the pharmaceutically acceptable salt thereof of the present invention may be administered alone or in combination with other active ingredients. The effective amounts of the N-aromatic amide compound with the formula (I) and/or (II) or the pharmaceutically acceptable salt thereof according to the invention can be determined by the person skilled in the art, for example, by the attending physician or the like using conventional methods. When determining the effective amount of the compound of the present invention, a number of factors should be considered by the attending physician, including, but not limited to: specific compound to be administered; administration in combination with other agents; type, size, age and general health of mammal; severity of disease; response of individual patient; route of administration; the characteristic of the bioavailability of the formulation administered; the selected dosage; the use of other concomitant drugs; and other relevant conditions. The regular dosage is 10-1000 mg.

DESCRIPTION OF THE EMBODIMENTS

The invention is further described in detail below by way of examples, which clearly represent only a part of the invention, instead of all of the invention. These examples are merely illustrative of the present invention and should not be understood as limitation to the protection scope of the invention. Based on the examples of the present invention, all other technical solutions obtained by those skilled in the art without paying creative labor are within the protection scope of the invention.

In the examples, the abbreviation THF stands for tetrahydrofuran, DMSO-$d_6$ stands for dimethyl sulfoxide-d6, DMSO stands for dimethyl sulphoxide, $CDCl_3$ stands for deuterated chloroform, eq stands for equivalent weight, HPLC stands for high pressure liquid chromatography, $PPh_3$ stands for triphenyl phosphine, $PCy_3$ stands for tricyclohexyl phosphine, $K_3PO_4$ stands for potassium phosphate tribasic, DMF stands for dimethylformamide, $Pd(PPh_3)_4$ stands for trtrakis(triphenyl phosphine)palladium, and DME stands for 1,2-dimethoxyethane.

The $^1$H NMR is determined by a Bruker AVANCE II 400 MHz NMR apparatus, wherein s stands for single peak, bs or brs stands for broad single peak, d stands for double peak, m stands for multiple peak, and Ar stands for aryl. Mass spectrum is determined by a Bruker amaZon SL Mass spectrometer. High resolution mass spectrum is determined by a Waters Acquity HPLC+Xeno G2-S TOF Mass. High pressure liquid chromatography is determined by a SHIMADZU CBM-20A. Thin layer chromatography is determined by a 60F254 silica gel plate (Merck).

I. EXAMPLES FOR PREPARING COMPOUNDS

Example 1

Preparation of N-(4-cyano-3-trifluoromethyl)-phenyl-2-[4-fluoro-6-(4-fluorophenyl)-1H-indolyl-1-yl]-2-methylpropanamide

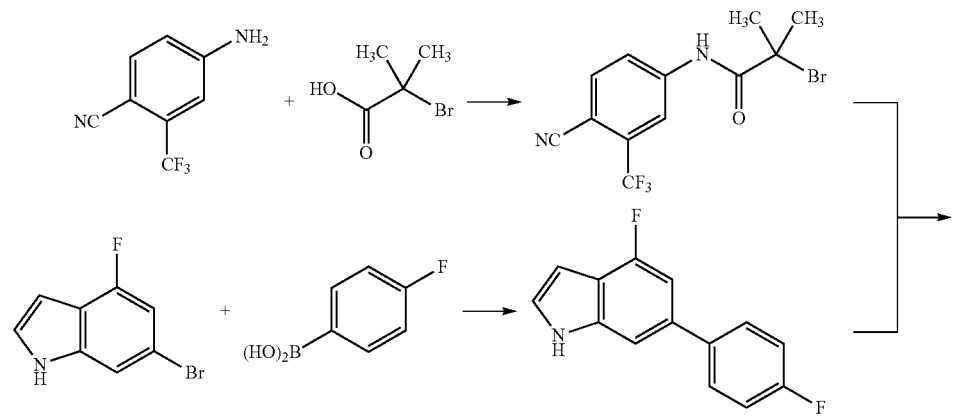

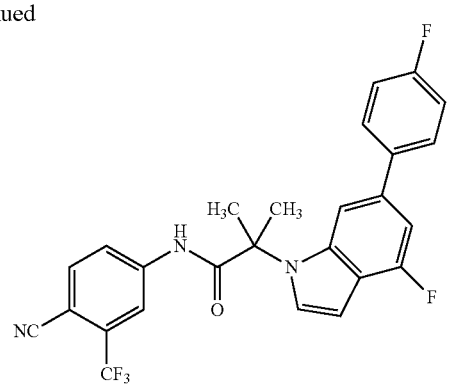

First Step of Reaction

Thionyl chloride (2.62 ml, 35.93 mmol, 1.2 eq) is added dropwise to a solution of 2-bromo-2-methyl propionic acid (5.00 g, 29.94 mmol) in 30 ml of anhydrous tetrahydrofuran (THF) at a temperature ranging from 0 to 12 Celsius degrees in 10 minutes. The resulting mixture is stirred under the same conditions for 2 hours. The internal temperature is adjusted to about −5 Celsius degrees. Triethylamine (Et$_3$N) (5.42 ml, 38.92 mmol, 1.3 eq) is slowly added to the reaction mixture, with an internal temperature lower than 12 Celsius degrees. The resulting mixture is stirred under the same reaction conditions for 20 minutes, and a solution of 4-cyano-3-trifluoromethyl-phenylamine (5.57 g, 29.94 mmol) in 30 mL of anhydrous tetrahydrofuran is then added dropwise thereto, and the resulting mixture is stirred at 50 Celsius degrees for two hours. After the reaction is completed as determined by thin layer chromatography, the reaction mixture is cooled to 20±5 Celsius degrees, water (50 ml) and ethyl acetate (50 ml) are then added thereto. The resulting mixture is shortly stirred and separated, with the organic phase washed by salt solution (30 ml), dried by magnesium sulphate, filtered, and with the resulting organic phase dried by suction to obtain an oily substance. The oily substance is separated and purified by silica gel column chromatography (mobile phase: hexane:ethyl acetate=2:1) to obtain 8.68 g of 2-bromo-N-(4-cyano-3-trifluoromethyl-phenyl)-2-methylpropanamide, with a yield of 86.8% and a purity of 99% by HPLC (mobile phase: water and acetonitrile) (254 nm).

Nuclear magnetic resonance spectrum: $^1$H NMR (400 MHz, DMSO-d$_6$) δ 10.57 (s, 1H, NH), 8.38 (s, 1H, ArH), 8.24 (d, J=8.4 Hz, 1H, ArH), 8.15 (d, J=8.4 Hz, 1H, ArH), 2.01 (s, 6H, 2×CH$_3$).

Mass spectrum: (ESI, Positive): 335.00[M+H]$^+$.

Second Step of Reaction 6-bromo-4-fluoro-1H-indole (1.00 g, 4.672 mmol) is added to a suspension of tetrakis (triphenyl phosphine) palladium ([Pd(PPh$_3$)$_4$] (0.54 g, 0.4672 mmol) in 20 ml of dimethoxyethane (DME). The resulting mixture is stirred under argon at room temperature for 15 minutes. A solution of 4-fluoro-phenylboronic acid (0.66 g, 4.672 mmol) in 2.5 ml of ethanol is added to the above reaction mixture, and the resulting mixture is stirred under the same conditions for 10 minutes. Potassium carbonate (0.92 g, 7.008 mmol) is then dissolved in 2.0 ml of water and added to the above reaction mixture. The resulting reaction mixture is heated to reflux under argon for 2-3 hours. After the reaction is completed as determined by thin layer chromatography, salt solution (20 ml) and ethyl acetate (30 ml) are added to the reaction mixture. The resulting mixture is shortly stirred and separated, with the organic phase washed by salt solution (15 ml), dried by magnesium sulphate, filtered, and with the resulting organic phase dried by suction to obtain an oily substance. The oily substance is separated and purified by silica gel column chromatography (mobile phase: hexane:ethyl acetate=3:1) to obtain 0.66 g of brown powdery material, identified as 4-fluoro-6-(4-fluorophenyl)-1H-indole, with a yield of about 62%.

Mass spectrum: (ESI, positive): 230.02[M+H]$^+$.

The Third Step of Reaction

In a 100 mL round bottom flask, 2-bromo-N-(4-cyano-3-trifluoromethyl-phenyl)-2-methylpropanamide (0.17 g, 0.500 mmol), 4-fluoro-6-(4-fluorophenyl)-1H-indole (0.22 g, 1.00 mmol), copper(I) bromide-dimethyl sulfide (11 mg, 0.05 mmol), triphenyl phosphine (PPh$_3$) (13 mg, 0.05 mmol), and sodium hydroxide (22 mg, 0.56 mmol) are added, with 10 mL of anhydrous methylbenzene as solvent. The resulting mixture is heated to 50 Celsius degrees and stirred under argon for 12 hours. After the reaction is completed as determined by thin layer chromatography, the reaction mixture is cooled to 20±5 Celsius degrees, water (30 ml) and ethyl acetate (30 ml) are then added thereto. The resulting mixture is shortly stirred and separated, with the organic phase washed by salt solution (20 ml), dried by magnesium sulphate, filtered, and with the resulting organic phase dried by suction to obtain an oily substance. The oily substance is separated and purified by silica gel column chromatography (mobile phase: hexane:ethyl acetate=3:1 to 2:1) to obtain 73 mg of yellow powdery material, identified as N-(4-cyano-3-trifluoromethyl)-phenyl-2-[4-fluoro-6-(4-fluorophenyl)-1H-indolyl-1-yl]-2-methylpropanamide, with a yield of 30%.

Nuclear magnetic resonance spectrum: $^1$H NMR (400 MHz, DMSO-d$_6$) δ10.43 (s, 1H, NH), 8.20 (d, J=2.0 Hz, 1H, ArH), 8.18-8.07 (m, 2H, ArH), 7.75 (d, J=3.6 Hz, 1H, indolyl-H), 7.52-7.48 (m, 2H, ArH), 7.27-7.22 (m, 2H, ArH), 7.17 (d, J=8.4 Hz, 1H, ArH), 7.14 (s, 1H, ArH), 6.68 (d, J=3.2 Hz, 1H, indolyl-H), 1.91 (s, 6H, 2×CH$_3$).

Mass spectrum: (ESI, Negative): 482.26 [M−H]$^-$.

Example 2

Preparation of N-(4-cyano-3-trifluoromethyl) phenyl-2-(5-fluoro-6-phenyl-1H-indolyl-1-yl)-2-methylpropanamide

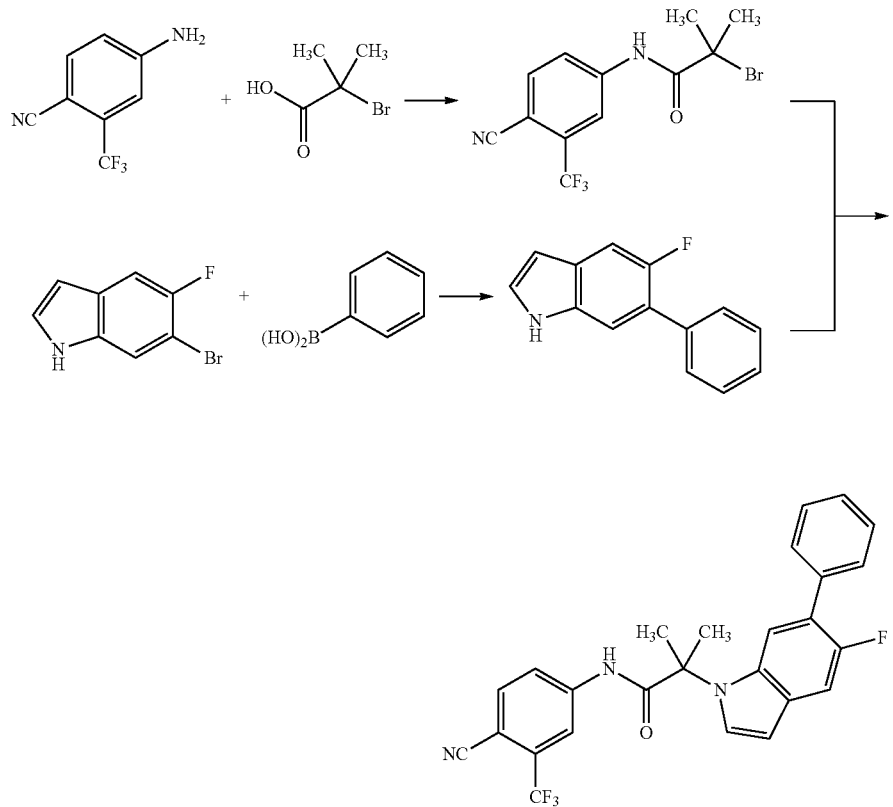

First Step of Reaction

The same as that of Example 1.

Second Step of Reaction 6-bromo-5-fluoro-1H-indole (1.00 g, 4.672 mmol) is added to a suspension of tetrakis (triphenyl phosphine) palladium ([Pd(PPh$_3$)$_4$] (0.54 g, 0.4672 mmol) in 20 ml of dimethoxyethane (DME). The resulting mixture is stirred under argon at room temperature for 15 minutes. A solution of phenylboronic acid (0.57 g, 4.672 mmol) in 2.5 ml of ethanol is added to the above reaction mixture, and the resulting mixture is stirred under the same conditions for 10 minutes. Potassium carbonate (0.97 g, 7.008 mmol) is then dissolved in 2.0 ml of water and added to the above reaction mixture. The resulting reaction mixture is heated to reflux under argon for 2-3 hours. After the reaction is completed as determined by thin layer chromatography, salt solution (20 ml) and ethyl acetate (30 ml) are added to the reaction mixture. The resulting mixture is shortly stirred and separated, with the organic phase washed by salt solution (15 ml), dried by magnesium sulphate, filtered, and with the resulting organic phase dried by suction to obtain an oily substance. The oily substance is separated and purified by silica gel column chromatography (mobile phase: hexane:ethyl acetate=3:1) to obtain 0.79 g of brown powdery material, identified as 5-fluoro-6-phenyl-1H-indole, with a yield of about 80%.

Mass spectrum: (ESI, positive): 212.03[M+H]$^+$.

The Third Step of Reaction

In a 100 mL round bottom flask, 2-bromo-N-(4-cyano-3-trifluoromethyl-phenyl)-2-methylpropanamide (0.32 g, 0.9468 mmol), 5-fluoro-6-phenyl-1H-indole (0.40 g, 1.8937 mmol), copper(I) bromide-dimethyl sulfide (20 mg, 0.18937 mmol), triphenyl phosphine (25 mg, 0.18937 mmol), and sodium hydroxide (42 mg, 1.0415 mmol) are added, with 10 mL of anhydrous methylbenzene as solvent. The resulting mixture is heated to 50 Celsius degrees and stirred under argon for 12 hours. After the reaction is completed as determined by thin layer chromatography, the reaction mixture is cooled to 20±5 Celsius degrees, water (30 ml) and ethyl acetate (30 ml) are then added thereto. The resulting mixture is shortly stirred and separated, with the organic phase washed by salt solution (20 ml), dried by magnesium sulphate, filtered, and with the resulting organic phase dried by suction to obtain an oily substance. The oily substance is separated and purified by silica gel column chromatography (mobile phase: hexane:ethyl acetate=2:1) to obtain 0.11 g of light brown powdery material, identified as N-(4-cyano-3-trifluoromethyl)-phenyl-2-[5-fluoro-6-phenyl-1H-indolyl-1-yl]-2-methylpropanamide, with a yield of 25%.

Nuclear magnetic resonance spectrum: $^1$H NMR (400 MHz, DMSO-d$_6$) δ10.43 (s, 1H, NH), 8.26 (s, 1H, ArH), 8.14-8.08 (m, 2H, ArH), 7.77 (d, J=3.2 Hz, 1H, indolyl-H), 7.50 (d, J=11.6 Hz, 1H), 7.42-7.33 (m, 3H, ArH), 7.30 (s, 1H), 7.28 (d, J=7.2 Hz, 1H), 7.13 (d, J=6.4 Hz, 1H), 6.62 (d, J=2.8 Hz, 1H, indolyl-H), 1.89 (s, 6H, 2×CH$_3$).

Mass spectrum: (ESI, Negative): 464.36 [M−H]$^−$.

Example 3

Preparation of N-(4-cyano-3-trifluoromethyl)-phenyl-2-(5-fluoro-1H-indolyl-1-yl)-2-methylpropanamide

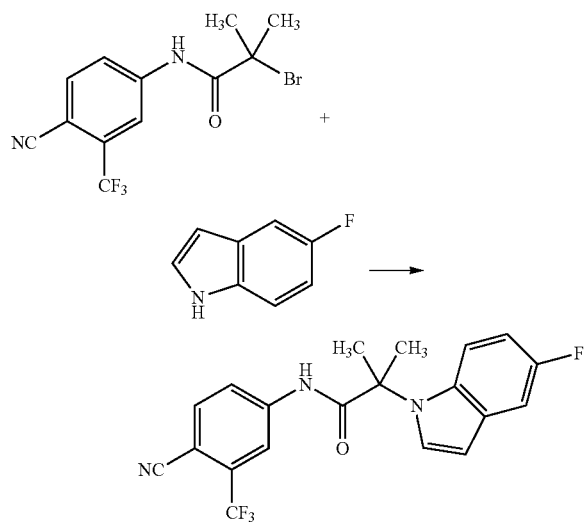

In a 100 mL round bottom flask, 2-bromo-N-(4-cyano-3-trifluoromethyl-phenyl)-2-methylpropanamide (0.20 g, 0.5968 mmol), 5-fluoro-1H-indole (0.16 g, 1.1963 mmol), copper(I) bromide-dimethyl sulfide (12.3 mg, 0.05868 mmol), triphenyl phosphine (15.7 mg, 0.05968 mmol), and sodium hydroxide (23.9 mg, 0.5968 mmol) are added, with 10 mL of anhydrous methylbenzene as solvent. The resulting mixture is heated to 50 Celsius degrees and stirred under argon for 12 hours. After the reaction is completed as determined by thin layer chromatography, the reaction mixture is cooled to 20±5 Celsius degrees, water (30 ml) and ethyl acetate (30 ml) are then added thereto. The resulting mixture is shortly stirred and separated, with the organic phase washed by salt solution (20 ml), dried by magnesium sulphate, filtered, and with the resulting organic phase dried by suction to obtain an oily substance. The oily substance is separated and purified by silica gel column chromatography (mobile phase: hexane:ethyl acetate=2:1) to obtain 0.13 g of light brown powdery material, identified as N-(4-cyano-3-trifluoromethyl)-phenyl-2-[5-fluoro-1H-indolyl-1-yl]-2-methylpropanamide, with a yield of 56%.

Nuclear magnetic resonance spectrum: $^1$H NMR (400 MHz, DMSO-$d_6$) δ10.29 (s, 1H, NH), 8.22 (d, J=2.0 Hz, 1H, ArH), 8.19 (dd, J=8.4 Hz, J=2.0 Hz, 1H, ArH), 8.09 (d, J=8.4 Hz, 1H, ArH), 7.71 (d, J=3.6 Hz, 1H, indolyl-H), 7.37 (dd, J=9.6 Hz, J=2.8 Hz, 1H), 7.12 (dd, J=9.2 Hz, J=4.0 Hz, 1H), 6.95 (dt, J=9.2 Hz, J=2.4 Hz, 1H), 6.57 (d, J=3.6 Hz, 1H, indolyl-H), 1.82 (s, 6H, 2×CH$_3$).

Mass spectrum: (ESI, Negative): 388.27 [M−H]$^−$.

Example 4

Preparation of N-(4-cyano-3-trifluoromethyl)-phenyl-2-(4-fluoro-1H-indolyl-1-yl)-2-methylpropanamide

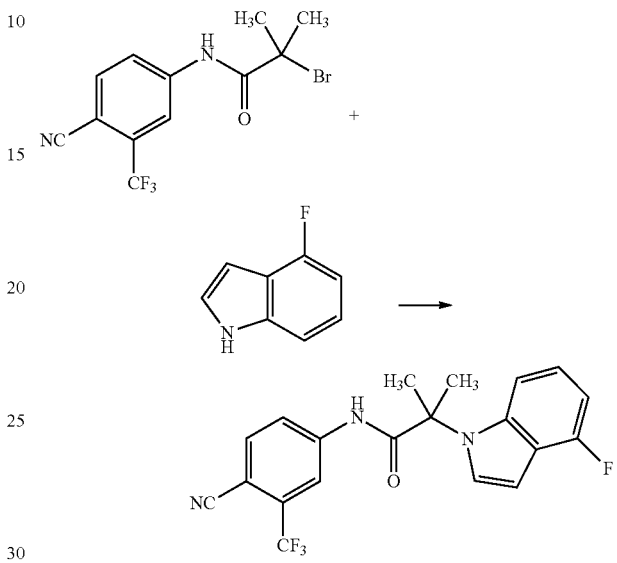

In a 100 mL round bottom flask, 2-bromo-N-(4-cyano-3-trifluoromethyl-phenyl)-2-methylpropanamide (0.20 g, 0.5968 mmol), 4-fluoro-1H-indole (0.16 g, 1.1963 mmol), copper(I) bromide-dimethyl sulfide (12.3 mg, 0.05868 mmol), triphenyl phosphine (15.7 mg, 0.05968 mmol), and sodium hydroxide (23.9 mg, 0.5968 mmol) are added, with 10 mL of anhydrous methylbenzene as solvent. The resulting mixture is heated to 50 Celsius degrees and stirred overnight under argon. After the reaction is completed as determined by thin layer chromatography, the reaction mixture is cooled to 20±5 Celsius degrees, water (30 ml) and ethyl acetate (30 ml) are then added thereto. The resulting mixture is shortly stirred and separated, with the organic phase washed by salt solution (20 ml), dried by magnesium sulphate, filtered, and with the resulting organic phase dried by suction to obtain an oily substance. The oily substance is separated and purified by silica gel column chromatography (mobile phase: hexane:ethyl acetate=2:1) to obtain 0.11 g of yellow powdery material, identified as N-(4-cyano-3-trifluoromethyl)-phenyl-2-[4-fluoro-1H-indolyl-1-yl]-2-methylpropanamide, with a yield of 47.3%.

Nuclear magnetic resonance spectrum: $^1$H NMR (400 MHz, CDCl$_3$) δ 7.90 (s, 1H, ArH), 7.72 (d, J=8.4 Hz, 1H, ArH), 7.50 (br s, 1H, NH), 7.38 (d, J=3.2 Hz, 1H, indolyl-H), 7.28 (m, 1H, ArH), 7.10 (d, J=8.4 Hz, 1H), 6.99 (dd, J=9.2 Hz, J=2.0 Hz, 1H), 6.77 (dd, J=9.2 Hz, J=2.0 Hz, 1H), 6.74 (d, J=2.8 Hz, 1H, indolyl-H), 1.93 (s, 6H, 2×CH$_3$).

Mass spectrum: (ESI, Negative): 388.26 [M−H]$^−$.

Example 5

Preparation of N-(4-cyano-3-trifluoromethyl)-phenyl-2-(6-fluoro-1H-indolyl-1-yl)-2-methylpropanamide

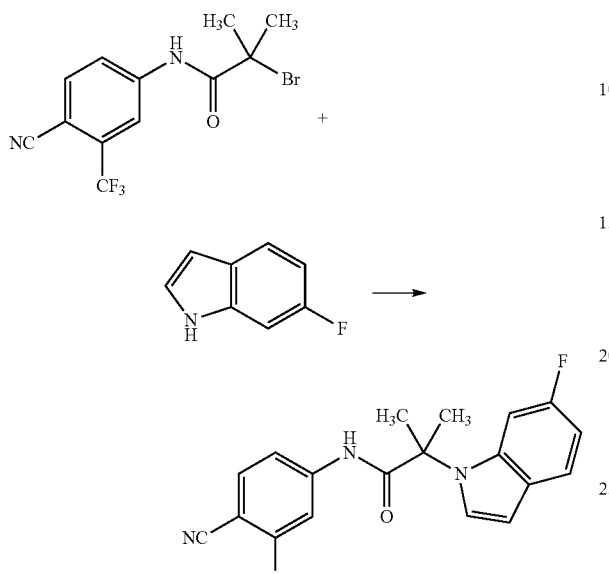

In a 100 mL round bottom flask, 2-bromo-N-(4-cyano-3-trifluoromethyl-phenyl)-2-methylpropanamide (0.20 g, 0.5968 mmol), 6-fluoro-1H-indole (0.16 g, 1.1963 mmol), copper(I) bromide-dimethyl sulfide (12.3 mg, 0.05868 mmol), triphenyl phosphine (15.7 mg, 0.05968 mmol), and sodium hydroxide ((23.9 mg, 0.5968 mmol) are added, with 10 mL of anhydrous methylbenzene as solvent. The resulting mixture is heated to 50 Celsius degrees and stirred overnight under argon. After the reaction is completed as determined by thin layer chromatography, the reaction mixture is cooled to 20±5 Celsius degrees, water (30 ml) and ethyl acetate (30 ml) are then added thereto. The resulting mixture is shortly stirred and separated, with the organic phase washed by salt solution (20 ml), dried by magnesium sulphate, filtered, and with the resulting organic phase dried by suction to obtain an oily substance. The oily substance is separated and purified by silica gel column chromatography (mobile phase: hexane:ethyl acetate=2:1) to obtain 0.12 g of yellow powdery material, identified as N-(4-cyano-3-trifluoromethyl)-phenyl-2-[6-fluoro-1H-indolyl-1-yl]-2-methylpropanamide, with a yield of 51.6%.

Nuclear magnetic resonance spectrum: $^1$H NMR (400 MHz, CDCl$_3$) δ 7.87 (d, J=1.6 Hz, 1H, ArH), 7.77 (d, J=8.4 Hz, 1H, ArH), 7.61 (dd, J=8.4 Hz, J=1.6 Hz, 1H, ArH), 7.51 (br s, 1H, NH), 7.35 (d, J=3.2 Hz, 1H, indolyl-H), 7.11 (dd, J=8.4H, J=4.0 Hz, 1H, ArH), 7.03 (dd, J=10.0 Hz, J=2.0 Hz, 1H), 6.84 (dd, J=8.8 Hz, J=2.2 Hz, 1H), 6.65 (d, J=3.0 Hz, 1H, indolyl-H), 1.95 (s, 6H, 2×CH$_3$).

Mass spectrum: (ESI, Negative): 388.30 [M–H]$^-$.

Example 6

Preparation of N-(4-cyano-3-trifluoromethyl)-phenyl-2-(5-nitro-1H-indolyl-1-yl)-2-methylpropanamide

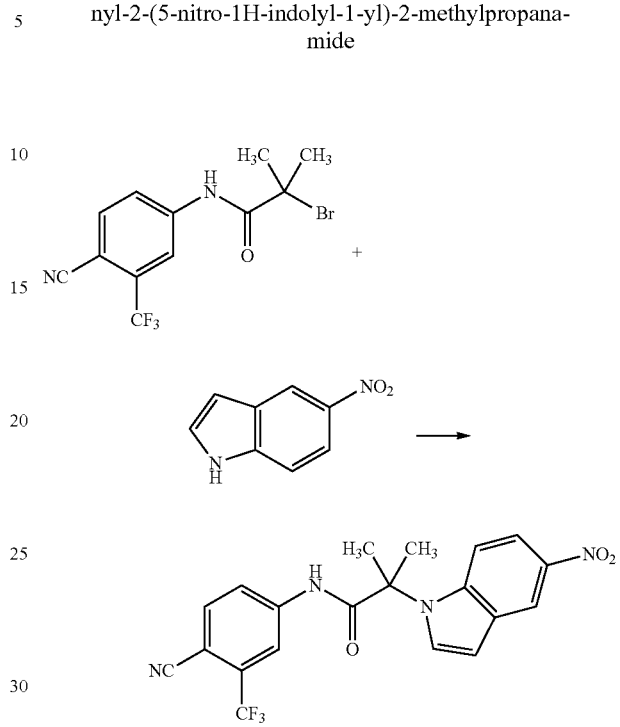

In a 100 mL round bottom flask, 2-bromo-N-(4-cyano-3-trifluoromethyl-phenyl)-2-methylpropanamide (0.20 g, 0.5968 mmol), 5-nitro-1H-indole (0.194 g, 1.1963 mmol), copper(I) bromide-dimethyl sulfide (12.3 mg, 0.05868 mmol), triphenyl phosphine (15.7 mg, 0.05968 mmol), and sodium hydroxide (24 mg, 0.5968 mmol) are added, with 10 mL of anhydrous methylbenzene as solvent. The resulting mixture is heated to 50 Celsius degrees and stirred overnight under argon. After the reaction is completed as determined by thin layer chromatography, the reaction mixture is cooled to 20±5 Celsius degrees, water (30 ml) and ethyl acetate (30 ml) are then added thereto. The resulting mixture is shortly stirred and separated, with the organic phase washed by salt solution (20 ml), dried by magnesium sulphate, filtered, and with the resulting organic phase dried by suction to obtain an oily substance. The oily substance is separated and purified by silica gel column chromatography (mobile phase: dichloromethane:ethyl acetate=9:1) to obtain 0.10 g of light brown powdery material, identified as N-(4-cyano-3-trifluoromethyl)-phenyl-2-[5-nitro-1H-indolyl-1-yl]-2-methylpropanamide, with a yield of 40.2%.

Nuclear magnetic resonance spectrum: $^1$H NMR (400 MHz, DMSO-d$_6$) δ 10.45 (s, 1H, NH), 8.24 (s, 1H, ArH), 8.19 (d, J=8.4 Hz, 1H, ArH), 8.09 (d, J=8.4 Hz, 1H, ArH), 7.85-7.81 (m, 3H), 7.50 (d, J=8.8 Hz, 1H), 6.70 (d, J=3.2 Hz, 1H, indolyl-H), 1.90 (s, 6H, 2×CH$_3$).

Mass spectrum: (ESI, Negative): 415.29 [M–H]$^-$.

Example 7

Preparation of N-(4-cyano-3-trifluoromethyl) phenyl-2-(5-chloro-1H-indolyl-1-yl)-2-methylpropanamide

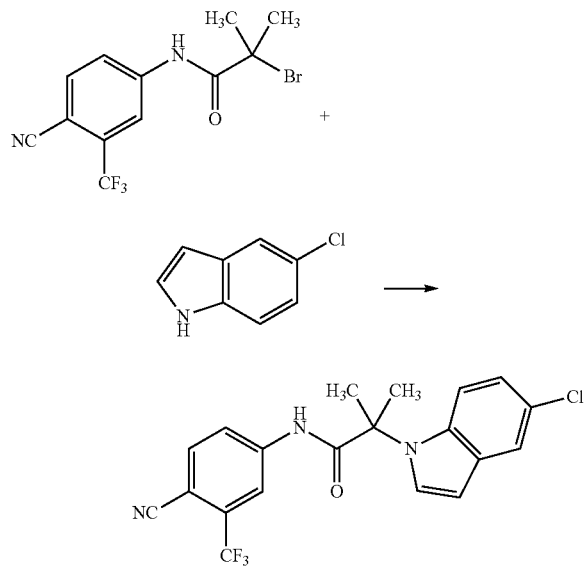

In a 100 mL round bottom flask, 2-bromo-N-(4-cyano-3-trifluoromethyl-phenyl)-2-methylpropanamide (0.20 g, 0.5968 mmol), 5-chloro-1H-indole (0.181 g, 1.1963 mmol), copper(I) bromide-dimethyl sulfide (12.3 mg, 0.05868 mmol), triphenyl phosphine (15.7 mg, 0.05968 mmol), and sodium hydroxide (24 mg, 0.5968 mmol) are added, with 10 mL of anhydrous methylbenzene as solvent. The resulting mixture is heated to 50 Celsius degrees and stirred overnight under argon. After the reaction is completed as determined by thin layer chromatography, the reaction mixture is cooled to 20±5 Celsius degrees, water (30 ml) and ethyl acetate (30 ml) are then added thereto. The resulting mixture is shortly stirred and separated, with the organic phase washed by salt solution (20 ml), dried by magnesium sulphate, filtered, and with the resulting organic phase dried by suction to obtain an oily substance. The oily substance is separated and purified by silica gel column chromatography (mobile phase: hexane:ethyl acetate=2:1) to obtain 0.13 g of yellow powdery material, identified as N-(4-cyano-3-trifluoromethyl)-phenyl-2-[5-chloro-1H-indolyl-1-yl]-2-methylpropanamide, with a yield of 53.7%.

Nuclear magnetic resonance spectrum: $^1$H NMR (400 MHz, DMSO-$d_6$) δ 10.36 (s, 1H, NH), 8.21 (d, J=2.0 Hz, 1H, ArH), 8.18 (dd, J=8.4 Hz, J=2.0 Hz, 1H, ArH), 8.07 (d, J=8.4 Hz, 1H, ArH), 7.73 (d, J=3.2 Hz, 1H, indolyl-H), 7.41 (s, 1H), 7.11-7.08 (m, 2H), 6.64 (d, J=3.2 Hz, 1H, indolyl-H), 1.84 (s, 6H, 2×CH$_3$).

Mass spectrum: (ESI, Negative): 403.12[M–H]$^-$.

Example 8

Preparation of N-(4-cyano-3-trifluoromethyl)-phenyl-2-(5-trifluoromethyl-1H-indolyl-1-yl)-2-methylpropanamide

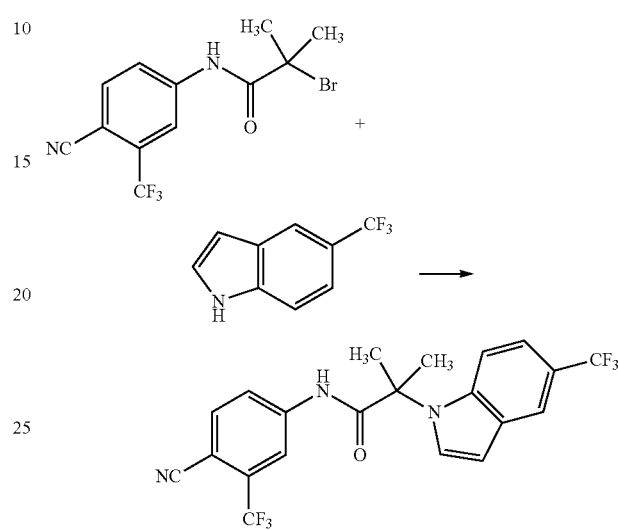

In a 100 mL round bottom flask, 2-bromo-N-(4-cyano-3-trifluoromethyl-phenyl)-2-methylpropanamide (0.20 g, 0.5968 mmol), 5-trifluoromethyl-1H-indole (0.22 g, 1.1963 mmol), copper(I) bromide-dimethyl sulfide (12.3 mg, 0.05868 mmol), triphenyl phosphine (15.7 mg, 0.05968 mmol), and sodium hydroxide (24 mg, 0.5968 mmol) are added, with 10 mL of anhydrous methylbenzene as solvent. The resulting mixture is heated to 50 Celsius degrees and stirred overnight under argon. After the reaction is completed as determined by thin layer chromatography, the reaction mixture is cooled to 20±5 Celsius degrees, water (30 ml) and ethyl acetate (30 ml) are then added thereto. The resulting mixture is shortly stirred and separated, with the organic phase washed by salt solution (20 ml), dried by magnesium sulphate, filtered, and with the resulting organic phase dried by suction to obtain an oily substance. The oily substance is separated and purified by silica gel column chromatography (mobile phase: hexane:ethyl acetate=2:1) to obtain 0.15 g of yellow powdery material, identified as N-(4-cyano-3-trifluoromethyl)-phenyl-2-[5-trifluoromethyl-1H-indolyl-1-yl]-2-methylpropanamide, with a yield of 57%.

Nuclear magnetic resonance spectrum: $^1$H NMR (400 MHz, DMSO-$d_6$) δ 10.35 (s, 1H, NH), 8.25 (d, J=1.6 Hz, 1H, ArH), 8.17 (dd, J=8.4 Hz, J=1.6 Hz, 1H, ArH), 8.10 (d, J=8.4 Hz, 1H, ArH), 7.78 (d, J=3.2 Hz, 1H, indolyl-H), 7.40 (m, 1H), 7.12-7.07 (m, 2H), 6.62 (d, J=3.2 Hz, 1H, indolyl-H), 1.87 (s, 6H, 2×CH$_3$).

Mass spectrum: (ESI, Negative): 438.25[M–H]$^-$.

Example 9

Preparation of N-(4-cyano-3-trifluoromethyl)-phenyl-2-(5-cyano-1H-indolyl-1-yl)-2-methylpropanamide

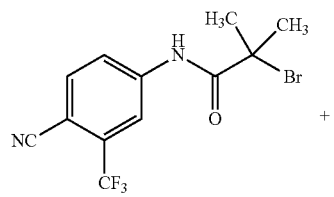

+

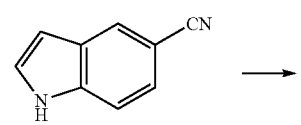

→

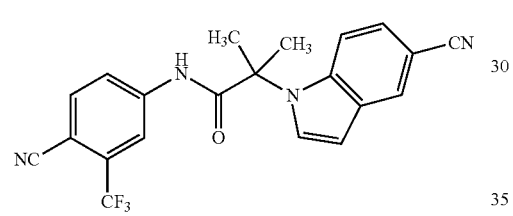

In a 100 mL round bottom flask, 2-bromo-N-(4-cyano-3-trifluoromethyl-phenyl)-2-methylpropanamide (0.20 g, 0.5968 mmol), 5-cyano-1H-indole (0.17 g, 1.1963 mmol), copper(I) bromide-dimethyl sulfide (12.3 mg, 0.05868 mmol), triphenyl phosphine (15.7 mg, 0.05968 mmol), and sodium hydroxide (24 mg, 0.5968 mmol) are added, with 10 mL of anhydrous methylbenzene as solvent. The resulting mixture is heated to 50 Celsius degrees and stirred overnight under argon. After the reaction is completed as determined by thin layer chromatography, the reaction mixture is cooled to 20±5 Celsius degrees, water (30 ml) and ethyl acetate (30 ml) are then added thereto. The resulting mixture is shortly stirred and separated, with the organic phase washed by salt solution (20 ml), dried by magnesium sulphate, filtered, and with the resulting organic phase dried by suction to obtain an oily substance. The oily substance is separated and purified by silica gel column chromatography (mobile phase: hexane:ethyl acetate=2:1) to obtain 90 mg of yellow powdery material, identified as N-(4-cyano-3-trifluoromethyl)-phenyl-2-(5-cyano-1H-indolyl-1-yl]-2-methylpropanamide, with a yield of 38%.

Nuclear magnetic resonance spectrum: $^1$H NMR (400 MHz, DMSO-$d_6$) δ 10.37 (s, 1H, NH), 8.27 (s, 1H, ArH), 8.19 (d, J=8.4 Hz, 1H, ArH), 8.05 (d, J=8.4 Hz, 1H, ArH), 7.78 (d, J=3.2 Hz, 1H, indolyl-H), 7.51 (d, J=8.6 Hz, 1H), 7.32 (d, J=8.6 Hz, 1H), 6.60 (d, J=3.2 Hz, 1H, indolyl-H), 1.85 (s, 6H, 2×CH$_3$).

Mass spectrum: (ESI, Negative): 395.20[M−H]$^−$.

Example 10

Preparation of N-(4-cyano-3-trifluoromethyl)-phenyl-2-(5-fluoro-1H-2,3-dihydroindolyl-1-yl)-2-methylpropanamide

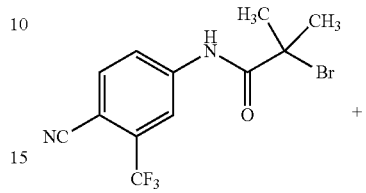

+

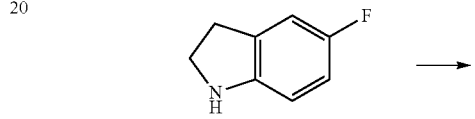

→

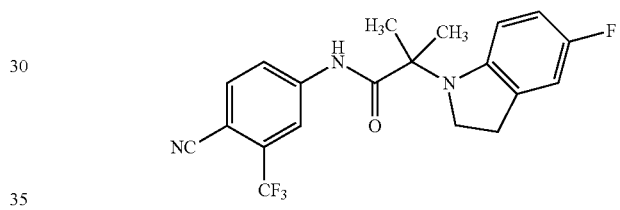

In a 100 mL round bottom flask, 2-bromo-N-(4-cyano-3-trifluoromethyl-phenyl)-2-methylpropanamide (0.20 g, 0.5968 mmol), 5-fluoro-1H-2,3-dihydroindole (0.163 g, 1.1963 mmol), copper(I) bromide-dimethyl sulfide (12.3 mg, 0.05868 mmol), tricyclohexyl phosphine (16.7 mg, 0.05968 mmol), tripotassium phosphate (0.152 g, 0.7162 mmol), and sodium hydroxide (24 mg, 0.5968 mmol) are added, with 10 mL of anhydrous methylbenzene as solvent. The resulting mixture is heated to 50 Celsius degrees and stirred overnight under argon. After the reaction is completed as determined by thin layer chromatography, the reaction mixture is cooled to 20±5 Celsius degrees, water (30 ml) and ethyl acetate (30 ml) are then added thereto. The resulting mixture is shortly stirred and separated, with the organic phase washed by salt solution (20 ml), dried by magnesium sulphate, filtered, and with the resulting organic phase dried by suction to obtain an oily substance. The oily substance is separated and purified by silica gel column chromatography (mobile phase: dichloromethane:ethyl acetate=9:1) to obtain 47 mg of yellow powdery material, identified as N-(4-cyano-3-trifluoromethyl)-phenyl-2-(5-fluoro-1H-2,3-dihydroindolyl-1-yl)-2-methylpropanamide, with a yield of 20%.

Nuclear magnetic resonance spectrum: $^1$H NMR (400 MHz, CDCl$_3$) δ 8.78 (s, 1H, NH), 7.95 (d, J=2.0 Hz, 1H, ArH), 7.60 (d, J=8.4 Hz, 1H, ArH), 7.41 (d, J=8.4 Hz, 1H, ArH), 6.85 (m, 1H), 6.41-6.37 (m, 2H), 3.36-3.33 (m, 1H), 3.10-3.04 (m, 2H), 2.98-2.95 (m, 1M), 1.87 (s, 6H, 2×CH$_3$).

Mass spectrum: (ESI, Negative): 390.29[M−H]$^−$.

Example 11

Preparation of N-(4-cyano-3-trifluoromethyl)-phenyl-2-(5,6-difluoro-1H-2,3-dihydroindolyl-1-yl)-2-methylpropanamide

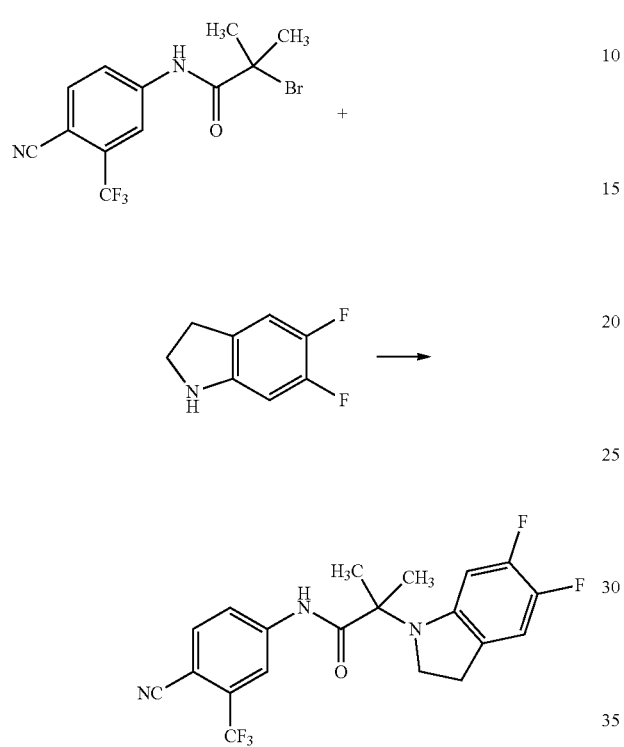

In a 100 mL round bottom flask, 2-bromo-N-(4-cyano-3-trifluoromethyl-phenyl)-2-methylpropanamide (0.20 g, 0.5968 mmol), 5,6-difluoro-1H-2,3-dihydroindole (0.185 g, 1.1963 mmol), copper(I) bromide-dimethyl sulfide (12.3 mg, 0.05868 mmol), tricyclohexyl phosphine (16.7 mg, 0.05968 mmol), tripotassium phosphate (0.152 g, 0.7162 mmol), and sodium hydroxide (24 mg, 0.5968 mmol) are added, with 10 mL of anhydrous methylbenzene as solvent. The resulting mixture is heated to 50 Celsius degrees and stirred overnight under argon. After the reaction is completed as determined by thin layer chromatography, the reaction mixture is cooled to 20±5 Celsius degrees, water (30 ml) and ethyl acetate (30 ml) are then added thereto. The resulting mixture is shortly stirred and separated, with the organic phase washed by salt solution (20 ml), dried by magnesium sulphate, filtered, and with the resulting organic phase dried by suction to obtain an oily substance. The oily substance is separated and purified by silica gel column chromatography (mobile phase: dichloromethane:ethyl acetate=9:1) to obtain 54 mg of yellow powdery material, identified as N-(4-cyano-3-trifluoromethyl)-phenyl-2-(5,6-difluoro-1H-2,3-dihydroindolyl-1-yl)-2-methylpropanamide, with a yield of 22%.

Nuclear magnetic resonance spectrum: $^1$H NMR (400 MHz, CDCl$_3$) δ 9.05 (br s, 1H, NH), 8.05 (d, J=2.0 Hz, 1H, ArH), 7.91 (dd, J=8.4 Hz, J=2.0 Hz, 1H, ArH), 7.64 (d, J=8.4 Hz, 1H, ArH), 6.68 (t, J=8.8 Hz, 1H), 6.39 (m, 1H), 3.42-3.37 (m, 2H), 3.02-2.94 (m, 2H), 1.88 (s, 6H, 2×CH$_3$).

Mass spectrum: (ESI, Negative): 408.28[M−H]$^-$.

Example 12

Preparation of N-(3-chloro-4-cyano) phenyl-2-(5-fluoro-1H-indolyl-1-yl)-2-methylpropanamide

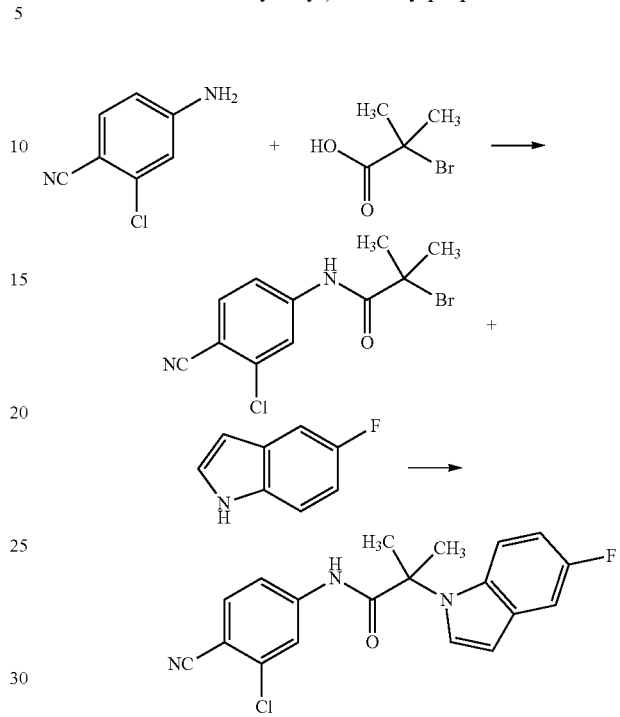

First Step of Reaction

Thionyl chloride (2.62 ml, 35.93 mmol, 1.2 eq) is added dropwise to a solution of 2-bromo-2-methyl propionic acid (5.00 g, 29.94 mmol) in 30 ml of anhydrous tetrahydrofuran at a temperature ranging from 0 to 12 Celsius degrees in 10 minutes. The resulting mixture is stirred under the same conditions for 2 hours. The internal temperature is adjusted to about −5 Celsius degrees. Triethylamine (Et$_3$N) (5.42 ml, 38.92 mmol, 1.3 eq) is slowly added to the reaction mixture, with an internal temperature lower than 12 Celsius degrees. The resulting mixture is stirred under the same reaction conditions for 20 minutes, and a solution of 3-chloro-4-cyano-phenylamine (4.57 g, 29.94 mmol) in 30 mL of anhydrous tetrahydrofuran is then added dropwise thereto, and the resulting mixture is stirred at 50 Celsius degrees for two hours. After the reaction is completed as determined by thin layer chromatography, the reaction mixture is cooled to 20±5 Celsius degrees, water (50 ml) and ethyl acetate (50 ml) are then added thereto. The resulting mixture is shortly stirred and separated, with the organic phase washed by salt solution (30 ml), dried by magnesium sulphate, filtered, and with the resulting organic phase dried by suction to obtain an oily substance. The oily substance is separated and purified by silica gel column chromatography (mobile phase: dichloromethane:ethyl acetate=19:1) to obtain 6.77 g of light yellow powdery material, identified as 2-bromo-N-(3-chloro-4-cyano-phenyl)-2-methylpropanamide, with a yield of 75% and a purity of 99% by HPLC (mobile phase: water and acetonitrile) (254 nm).

Nuclear magnetic resonance spectrum: $^1$H NMR (400 MHz, DMSO-d$_6$) δ 10.43 (s, 1H, NH), 8.43 (s, 1H, ArH), 8.34 (d, J=8.6 Hz, 1H, ArH), 8.28 (d, J=8.6 Hz, 1H, ArH), 2.05 (s, 6H, 2×CH$_3$).

Mass spectrum: (ESI, Positive): 301.02[M+H]$^+$.

Second Step of Reaction

In a 100 mL round bottom flask, 2-bromo-N-(3-chloro-4-cyano-phenyl)-2-methylpropanamide (0.30 g, 0.9948 mmol), (5-fluoro-phenyl)-1H-indole (0.269 g, 1.9896 mmol), copper(I) bromide-dimethyl sulfide (20.5 mg, 0.0994 mmol), triphenyl phosphine (26.1 mg, 0.09948 mmol), tripotassium phosphate (0.25 g, 1.1938 mmol), and sodium hydroxide (44 mg, 0.56 mmol) are added, with 10 mL of anhydrous methylbenzene as solvent. The resulting mixture is heated to 50 Celsius degrees and stirred under argon for 14 hours. After the reaction is completed as determined by thin layer chromatography, the reaction mixture is cooled to 20±5 Celsius degrees, water (30 ml) and ethyl acetate (30 ml) are then added thereto. The resulting mixture is shortly stirred and separated, with the organic phase washed by salt solution (20 ml), dried by magnesium sulphate, filtered, and with the resulting organic phase dried by suction to obtain an oily substance. The oily substance is separated and purified by silica gel column chromatography (mobile phase: dichloromethane:ethyl acetate=19:1 to 9:1) to obtain 0.145 g of yellow powdery material, identified as N-(3-chloro-4-cyano) phenyl-2-[5-fluoro-1H-indolyl-1-yl]-2-methylpropanamide, with a yield of 41%.

Nuclear magnetic resonance spectrum: $^1$H NMR (400 MHz, CDCl$_3$) δ 8.60 (br s, 1H, NH), 7.79 (d, J=2.0 Hz, 1H, ArH), 7.52 (d, J=8.4 Hz, 1H, ArH), 7.38-7.26 (m, 2H), 7.22-7.18 (m, 3H), 6.61 (d, J=3.2 Hz, 1H, indolyl-H), 1.90 (s, 6H, 2×CH$_3$).

Mass spectrum: (ESI, Negative): 354.02 [M−H]$^-$.

Example 13

Preparation of N-(4-cyano-3-trifluoromethyl)-phenyl-2-[3-fluoro-4-(4-fluorophenyl)-1H-pyrazolyl-1-yl]-2-methylpropanamide and potassium carbonate (3.36 g, 24.248 mmol) are added, with 20 mL of ethazine and 10 mL of water as solvent. The resulting mixture is heated to reflux and stirred under argon for 3-4 hours. After the reaction is completed as determined by thin layer chromatography, water (30 ml) and ethyl acetate (30 ml) are added to the reaction mixture. The resulting mixture is shortly stirred and separated, with the organic phase washed by salt solution (30 ml), dried by magnesium sulphate, filtered, and with the resulting organic phase dried by suction to obtain an oily substance. The oily substance is separated and purified by silica gel column chromatography (mobile phase: hexane:ethyl acetate=2:1 to 1:1) to obtain 0.66 g of light yellow powdery material, identified as 3-fluoro-4-(4-fluorophenyl)-1H-pyrazole, with a yield of 30%.

Mass spectrum: (ESI, positive): 181.07[M+H]$^+$.

The Third Step of Reaction

In a 100 mL round bottom flask, 2-bromo-N-(4-cyano-3-trifluoromethyl-phenyl)-2-methylpropanamide (0.40 g, 1.1936 mmol), 3-fluoro-4-(4-fluorophenyl)-1H-pyrazole (0.43 g, 2.38727 mmol), copper(I) bromide-dimethyl sulfide (25 mg, 0.11936 mmol), triphenyl phosphine (31 mg, 0.11936 mmol), tripotassium phosphate (0.304 g, 1.4323 mmol) and sodium hydroxide (53 mg, 1.3130 mmol) are added, with 10 mL of anhydrous methylbenzene as solvent. The resulting mixture is heated to 50 Celsius degrees and stirred under argon for 12 hours. After the reaction is completed as determined by thin layer chromatography, the reaction mixture is cooled to 20±5 Celsius degrees, water (30 ml) and ethyl acetate (35 ml) are then added thereto. The resulting mixture is shortly stirred and separated, with the organic phase washed by salt solution (25 ml), dried by magnesium sulphate, filtered, and with the resulting organic phase dried by suction to obtain an oily substance. The oily substance is separated and purified by silica gel column

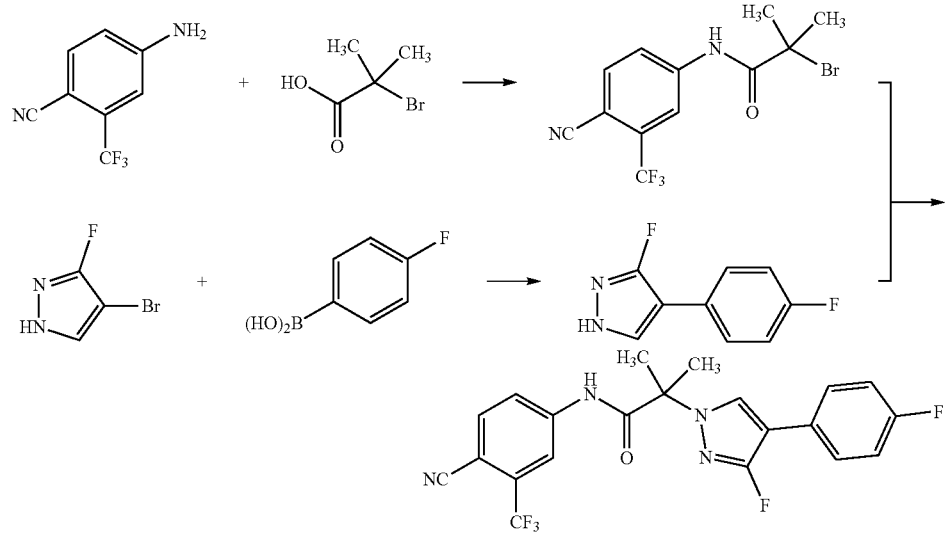

First Step of Reaction

The same as that of Example 1.

Second Step of Reaction

In a 100 mL round bottom flask, 3-fluoro-4-bromo-1H-pyrazole (2.00 g, 12.124 mmol), 4-fluoro-phenylboronic acid (2.04 g, 14.549 mmol), palladium (II) acetate (54 mg, 0.2424 mmol), triphenyl phosphine (0.128 g, 0.483 mmol), chromatography (mobile phase: hexane:ethyl acetate=3:1 to 2:1) to obtain 0.26 g of light yellow powdery material, identified as N-(4-cyano-3-trifluoromethyl)-phenyl-2-[3-fluoro-4-(4-fluorophenyl)-1H-pyrazolyl-1-yl]-2-methylpropanamide, with a yield of 50%.

Nuclear magnetic resonance spectrum: $^1$H NMR (400 MHz, DMSO-d$_6$) 510.14 (s, 1H, NH), 8.33 (d, J=1.6 Hz, 1H, ArH), 8.21 (dd, J=8.2 Hz, J=1.6 Hz, 1H, ArH), 8.11 (d, J=8.2 Hz, 1H, ArH), 8.05 (d, J=3.0 Hz, 1H, pyrazolyl-H), 7.86-7.82 (m, 2H), 7.25-7.21 (m, 2H), 1.86 (s, 6H, 2×CH₃).

Mass spectrum: (ESI, Negative): 433.27 [M–H]⁻.

Example 14

The Preparation of N-(4-cyano-3-trifluoromethyl)-phenyl-2-[4-(4-fluorophenyl)-1H-pyrazolyl-1-yl]-2-methylpropanamide

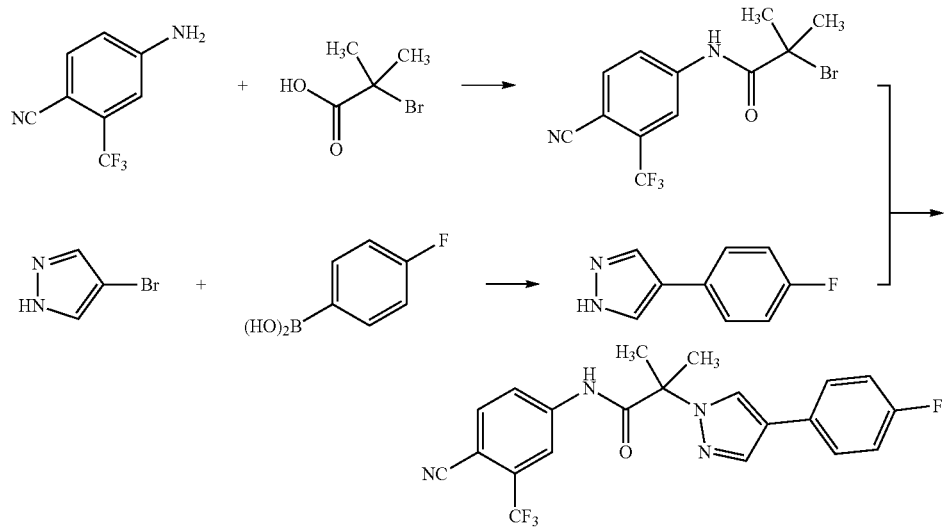

First Step of Reaction
The same as that of Example 1.
Second Step of Reaction
In a 100 mL round bottom flask, 4-bromo-1H-pyrazole (1.00 g, 6.8041 mmol), 4-fluoro-phenylboronic acid (1.14 g, 8.1649 mmol), palladium (II) acetate (30 mg, 0.1361 mmol), triphenyl phosphine (71.4 g, 0.2722 mmol), and potassium carbonate (1.88 g, 13.6082 mmol) are added, with 20 mL of ethazine and 10 mL of water as solvent. The resulting mixture is heated to reflux and stirred under argon for 3-4 hours. After the reaction is completed as determined by thin layer chromatography, water (30 ml) and ethyl acetate (30 ml) are added to the reaction mixture. The resulting mixture is shortly stirred and separated, with the organic phase washed by salt solution (30 ml), dried by magnesium sulphate, filtered, and with the resulting organic phase dried by suction to obtain an oily substance. The oily substance is separated and purified by silica gel column chromatography (mobile phase: hexane:ethyl acetate=2:1 to 1:1) to obtain 0.55 g of light yellow powdery material, identified as 4-(4-fluorophenyl)-1H-pyrazole, with a yield of 50%.

Mass spectrum: (ESI, positive): 163.02[M+H]⁺.

The Third Step of Reaction
In a 100 mL round bottom flask, 2-bromo-N-(4-cyano-3-trifluoromethyl-phenyl)-2-methylpropanamide (0.40 g, 1.1936 mmol), 4-(4-fluorophenyl)-1H-pyrazole (0.39 g, 2.38727 mmol), copper(I) bromide-dimethyl sulfide (25 mg, 0.11936 mmol), triphenyl phosphine (31 mg, 0.11936 mmol), tripotassium phosphate (0.304 g, 1.4323 mmol) and sodium hydroxide (53 mg, 1.3130 mmol) are added, with 10 mL of anhydrous methylbenzene as solvent. The resulting mixture is heated to 50 Celsius degrees and stirred under argon for 12 hours. After the reaction is completed as determined by thin layer chromatography, the reaction mixture is cooled to 20±5 Celsius degrees, water (30 ml) and ethyl acetate (35 ml) are then added thereto. The resulting mixture is shortly stirred and separated, with the organic phase washed by salt solution (25 ml), dried by magnesium sulphate, filtered, and with the resulting organic phase dried by suction to obtain an oily substance. The oily substance is separated and purified by silica gel column chromatography (mobile phase: hexane:ethyl acetate=3:1 to 2:1) to obtain 0.28 g of white powdery material, identified as N-(4-cyano-3-trifluoromethyl)-phenyl-2-[4-(4-fluorophenyl)-1H-pyrazolyl-1-yl]-2-methylpropanamide, with a yield of 56.4%.

Nuclear magnetic resonance spectrum: ¹H NMR (400 MHz, DMSO-d₆) δ10.12 (s, 1H, NH), 8.31 (d, J=2.0 Hz, 1H, ArH), 8.18 (dd, J=8.4 Hz, J=2.0 Hz, 1H, ArH), 8.10 (d, J=8.4 Hz, 1H, ArH), 8.03 (d, J=3.0 Hz, 1H, pyrazolyl-H), 7.84-7.80 (m, 2H), 7.23-7.19 (m, 2H), 1.86 (s, 6H, 2×CH₃).

Mass spectrum: (ESI, Negative): 415.27 [M–H]⁻.

Example 15

Preparation of N-(4-cyano-3-trifluoromethyl)-phenyl-2-(4-fluoro-1H-pyrazolyl-1-yl)-2-methylpropanamide

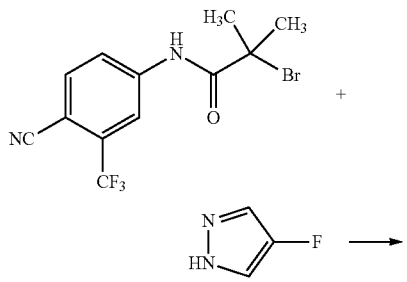

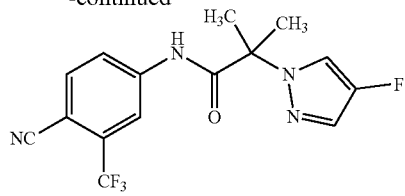

In a 100 mL round bottom flask, 2-bromo-N-(4-cyano-3-trifluoromethyl-phenyl)-2-methylpropanamide (0.40 g, 1.1936 mmol), 4-fluoro-1H-pyrazole (0.21 g, 2.38727 mmol), copper(I) bromide-dimethyl sulfide (25 mg, 0.11936 mmol), triphenyl phosphine (31 mg, 0.11936 mmol), tripotassium phosphate (0.304 g, 1.4323 mmol) and sodium hydroxide (53 mg, 1.3130 mmol) are added, with 10 mL of anhydrous methylbenzene as solvent. The resulting mixture is heated to 50 Celsius degrees and stirred under argon for 12 hours. After the reaction is completed as determined by thin layer chromatography, the reaction mixture is cooled to 20±5 Celsius degrees, water (30 ml) and ethyl acetate (35 ml) are then added thereto. The resulting mixture is shortly stirred and separated, with the organic phase washed by salt solution (25 ml), dried by magnesium sulphate, filtered, and with the resulting organic phase dried by suction to obtain an oily substance. The oily substance is separated and purified by silica gel column chromatography (mobile phase: hexane:ethyl acetate=3:1 to 2:1) to obtain 0.15 g of white powdery material, identified as N-(4-cyano-3-trifluoromethyl)-phenyl-2-(4-fluoro-1H-pyrazolyl-1-yl)-2-methylpropanamide, with a yield of 37%.

Nuclear magnetic resonance spectrum: $^1$H NMR (400 MHz, DMSO-$d_6$) δ10.05 (s, 1H, NH), 8.27 (d, J=2.0 Hz, 1H, ArH), 8.16 (dd, J=8.4 Hz, J=2.0 Hz, 1H, ArH), 8.14 (d, J=4.4 Hz, 1H, 吡唑-H), 8.10 (d, J=8.4 Hz, 1H, ArH), 7.57 (d, J=4.0 Hz, 1H, pyrazolyl-H), 1.77 (s, 6H, 2×CH$_3$).

Mass spectrum: (ESI, Negative): 339.26 [M–H]$^-$.

Example 16

Preparation of N-(4-cyano-3-trifluoromethyl)-phenyl-2-(3-fluoro-1H-pyrazolyl-1-yl)-2-methylpropanamide

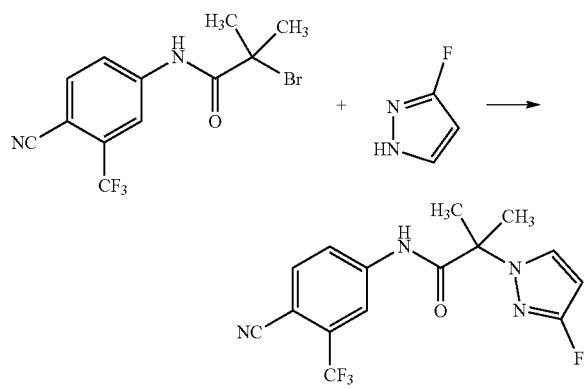

In a 100 mL round bottom flask, 2-bromo-N-(4-cyano-3-trifluoromethyl-phenyl)-2-methylpropanamide (0.40 g, 1.1936 mmol), 3-fluoro-1H-pyrazole (0.21 g, 2.38727 mmol), copper(I) bromide-dimethyl sulfide (25 mg, 0.11936 mmol), triphenyl phosphine (31 mg, 0.11936 mmol), tripotassium phosphate (0.304 g, 1.4323 mmol) and sodium hydroxide (53 mg, 1.3130 mmol) are added, with 10 mL of anhydrous methylbenzene as solvent. The resulting mixture is heated to 50 Celsius degrees and stirred under argon for 12 hours. After the reaction is completed as determined by thin layer chromatography, the reaction mixture is cooled to 20±5 Celsius degrees, water (30 ml) and ethyl acetate (35 ml) are then added thereto. The resulting mixture is shortly stirred and separated, with the organic phase washed by salt solution (25 ml), dried by magnesium sulphate, filtered, and with the resulting organic phase dried by suction to obtain an oily substance. The oily substance is separated and purified by silica gel column chromatography (mobile phase: hexane:ethyl acetate=3:1 to 2:1) to obtain 0.12 g of white powdery material, identified as N-(4-cyano-3-trifluoromethyl)-phenyl-2-(3-fluoro-1H-pyrazolyl-1-yl)-2-methylpropanamide, with a yield of 30%.

Nuclear magnetic resonance spectrum: $^1$H NMR (400 MHz, DMSO-$d_6$) δ10.05 (s, 1H, NH), 8.27 (d, J=2.0 Hz, 1H, ArH), 8.16 (dd, J=8.4 Hz, J=2.0 Hz, 1H, ArH), 8.10 (d, J=8.4 Hz, 1H, ArH), 7.95 (d, J=3.0 Hz, 1H, pyrazolyl-H), 6.11 (m, 1H), 1.79 (s, 6H, 2×CH$_3$).

Mass spectrum: (ESI, Negative): 339.25 [M–H]$^-$.

Example 17

Preparation of N-(4-cyano-3-trifluoromethyl)-phenyl-2-(4-chloro-1H-pyrazolyl-1-yl)-2-methylpropanamide

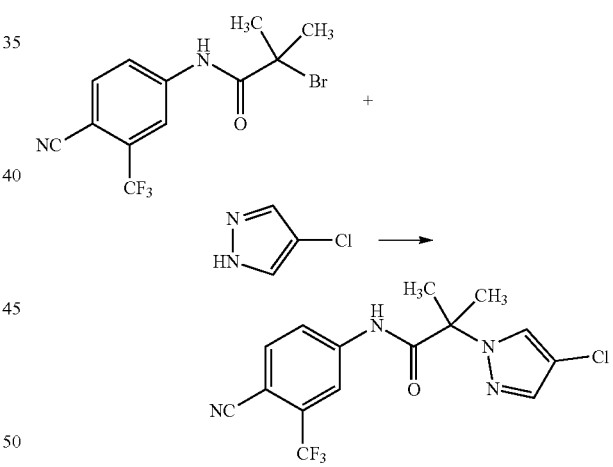

In a 100 mL round bottom flask, 2-bromo-N-(4-cyano-3-trifluoromethyl-phenyl)-2-methylpropanamide (0.40 g, 1.1936 mmol), 4-chloro-1H-pyrazole (0.245 g, 2.38727 mmol), copper(I) bromide-dimethyl sulfide (25 mg, 0.11936 mmol), triphenyl phosphine (31 mg, 0.11936 mmol), tripotassium phosphate (0.304 g, 1.4323 mmol) and sodium hydroxide (53 mg, 1.3130 mmol) are added, with 10 mL of anhydrous methylbenzene as solvent. The resulting mixture is heated to 50 Celsius degrees and stirred under argon for 14 hours. After the reaction is completed as determined by thin layer chromatography, the reaction mixture is cooled to 20±5 Celsius degrees, water (30 ml) and ethyl acetate (35 ml) are then added thereto. The resulting mixture is shortly stirred and separated, with the organic phase washed by salt solution (25 ml), dried by magnesium sulphate, filtered, and with the resulting organic phase dried by suction to obtain an oily substance. The oily substance is separated and purified by silica gel column chromatography (mobile phase: hexane:ethyl acetate=3:1 to 2:1) to obtain 0.233 g of white powdery material, identified as N-(4-cyano-3-trifluoromethyl)-phenyl-2-(4-chloro-1H-pyrazolyl-1-yl)-2-methylpropanamide, with a yield of 55%.

Nuclear magnetic resonance spectrum: $^1$H NMR (400 MHz, DMSO-$d_6$) δ10.04 (s, 1H, NH), 8.26 (s, 1H, ArH), 8.23 (s, 1H, pyrazolyl-H), 8.15 (d, J=8.6 Hz, 1H, ArH), 8.10 (d, J=8.6 Hz, 1H, ArH), 7.36 (s, 1H, pyrazolyl-H), 1.79 (s, 6H, 2×CH$_3$).

Mass spectrum: (ESI, Negative): 355.08[M−H]$^-$.

Example 18

Preparation of N-(4-cyano-3-trifluoromethyl)-phenyl-2-(4-trifluormethyl-1H-pyrazolyl-1-yl)-2-methylpropanamide

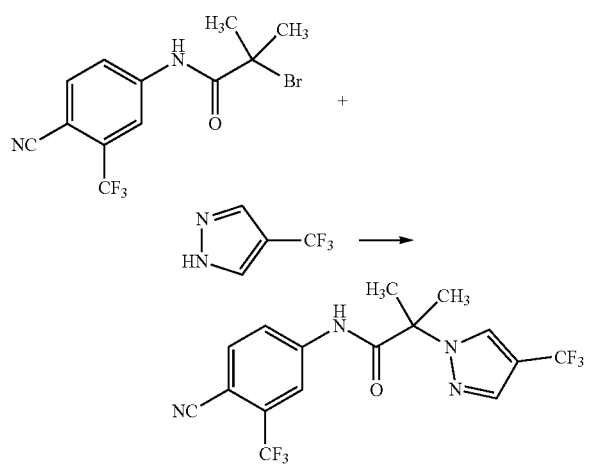

In a 100 mL round bottom flask, 2-bromo-N-(4-cyano-3-trifluoromethyl-phenyl)-2-methylpropanamide (0.40 g, 1.1936 mmol), 4-trifluoromethyl-1H-pyrazole (0.325 g, 2.38727 mmol), copper(I) bromide-dimethyl sulfide (25 mg, 0.11936 mmol), triphenyl phosphine (31 mg, 0.11936 mmol), tripotassium phosphate (0.304 g, 1.4323 mmol) and sodium hydroxide (53 mg, 1.3130 mmol) are added, with 10 mL of anhydrous methylbenzene as solvent. The resulting mixture is heated to 50 Celsius degrees and stirred under argon for 14 hours. After the reaction is completed as determined by thin layer chromatography, the reaction mixture is cooled to 20±5 Celsius degrees, water (30 ml) and ethyl acetate (35 ml) are then added thereto. The resulting mixture is shortly stirred and separated, with the organic phase washed by salt solution (25 ml), dried by magnesium sulphate, filtered, and with the resulting organic phase dried by suction to obtain an oily substance. The oily substance is separated and purified by silica gel column chromatography (mobile phase: hexane:ethyl acetate=2:1) to obtain 0.144 g of white powdery material, identified as N-(4-cyano-3-trifluoromethyl)-phenyl-2-(4-trifluoromethyl-1H-pyrazolyl-1-yl)-2-methylpropanamide, with a yield of 31%.

Nuclear magnetic resonance spectrum: $^1$H NMR (400 MHz, DMSO-$d_6$) δ10.04 (s, 1H, NH), 8.42 (s, 1H, pyrazolyl-H), 8.25 (d, J=2.0 Hz, 1H, ArH), 8.17 (dd, J=8.2 Hz, J=2.0 Hz, 1H, ArH), 8.11 (d, J=8.2 Hz, 1H, ArH), 7.90 (s, 1H, pyrazolyl-H), 1.85 (s, 6H, 2×CH$_3$).

Mass spectrum: (ESI, Negative): 389.21[M−H]$^-$.

Example 19

Preparation of N-(4-cyano-3-trifluoromethyl)-phenyl-2-(4-nitro-1H-pyrazolyl-1-yl)-2-methylpropanamide

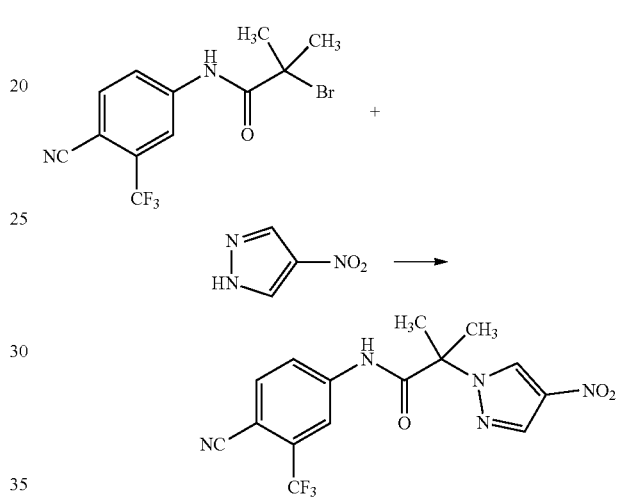

In a 100 mL round bottom flask, 2-bromo-N-(4-cyano-3-trifluoromethyl-phenyl)-2-methylpropanamide (0.40 g, 1.1936 mmol), 4-nitro-1H-pyrazole (0.27 g, 2.38727 mmol), copper(I) bromide-dimethyl sulfide (25 mg, 0.11936 mmol), triphenyl phosphine (31 mg, 0.11936 mmol), tripotassium phosphate (0.304 g, 1.4323 mmol) and sodium hydroxide (53 mg, 1.3130 mmol) are added, with 10 mL of anhydrous methylbenzene as solvent. The resulting mixture is heated to 50 Celsius degrees and stirred overnight under argon. After the reaction is completed as determined by thin layer chromatography, the reaction mixture is cooled to 20±5 Celsius degrees, water (30 ml) and ethyl acetate (35 ml) are then added thereto. The resulting mixture is shortly stirred and separated, with the organic phase washed by salt solution (25 ml), dried by magnesium sulphate, filtered, and with the resulting organic phase dried by suction to obtain an oily substance. The oily substance is separated and purified by silica gel column chromatography (mobile phase: hexane:ethyl acetate=2:1) to obtain 0.17 g of light yellow powdery material, identified as N-(4-cyano-3-trifluoromethyl)-phenyl-2-(4-nitro-1H-pyrazolyl-1-yl)-2-methylpropanamide, with a yield of 39%.

Nuclear magnetic resonance spectrum: $^1$H NMR (400 MHz, DMSO-$d_6$) δ10.02 (s, 1H, NH), 8.88 (s, 1H, pyrazolyl-H), 8.34 (s, 1H, pyrazolyl-H), 8.25 (d, J=1.2 Hz, 1H, ArH), 8.16 (dd, J=8.6 Hz, J=1.2 Hz, 1H, ArH), 8.11 (d, J=8.6 Hz, 1H, ArH), 1.84 (s, 6H, 2×CH$_3$).

Mass spectrum: (ESI, Negative): 366.19[M−H]$^-$.

Example 20

Preparation of N-(4-cyano-3-trifluoromethyl)-phenyl-2-(4-cyano-1H-pyrazolyl-1-yl)-2-methylpropanamide

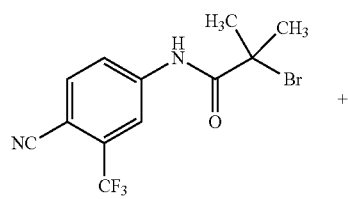

In a 100 mL round bottom flask, 2-bromo-N-(4-cyano-3-trifluoromethyl-phenyl)-2-methylpropanamide (0.40 g, 1.1936 mmol), 4-cyano-1H-pyrazole (0.222 g, 2.38727 mmol), copper(I) bromide-dimethyl sulfide (25 mg, 0.11936 mmol), triphenyl phosphine (31 mg, 0.11936 mmol), tripotassium phosphate (0.304 g, 1.4323 mmol) and sodium hydroxide (53 mg, 1.3130 mmol) are added, with 10 mL of anhydrous methylbenzene as solvent. The resulting mixture is heated to 50 Celsius degrees and stirred overnight under argon. After the reaction is completed as determined by thin layer chromatography, the reaction mixture is cooled to 20±5 Celsius degrees, water (30 ml) and ethyl acetate (35 ml) are then added thereto. The resulting mixture is shortly stirred and separated, with the organic phase washed by salt solution (25 ml), dried by magnesium sulphate, filtered, and with the resulting organic phase dried by suction to obtain an oily substance. The oily substance is separated and purified by silica gel column chromatography (mobile phase: hexane:ethyl acetate=2:1 to 1:1) to obtain 0.182 g of light yellow powdery material, identified as N-(4-cyano-3-trifluoromethyl)-phenyl-2-(4-cyano-1H-pyrazolyl-1-yl)-2-methylpropanamide, with a yield of 45%.

Nuclear magnetic resonance spectrum: $^1$H NMR (400 MHz, DMSO-$d_6$) δ10.01 (s, 1H, NH), 8.63 (s, 1H, pyrazolyl-H), 8.25 (d, J=1.2 Hz, 1H, ArH), 8.14 (dd, J=8.8 Hz, J=1.2 Hz, 1H, ArH), 8.13 (s, 1H, pyrazolyl-H), 8.10 (d, J=8.8 Hz, 1H, ArH), 1.82 (s, 6H, 2×CH$_3$).

Mass spectrum: (ESI, Negative): 346.23[M−H]$^-$.

Example 21

Preparation of 1-{1-[(4-cyano-3-trifluoromethyl-phenyl)-amino]-2-methyl-1-oxopropyl-2-yl}-N-methyl-1H-pyrazolyl-4-formamide

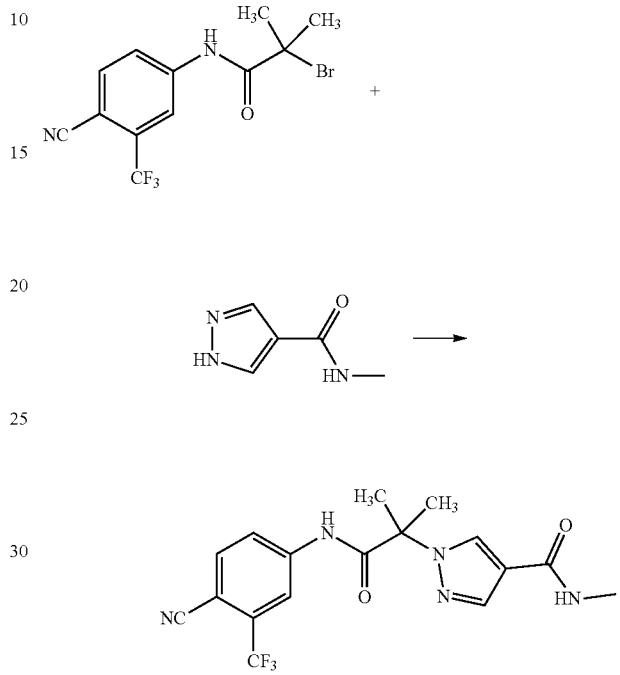

In a 100 mL round bottom flask, 2-bromo-N-(4-cyano-3-trifluoromethyl-phenyl)-2-methylpropanamide (0.40 g, 1.1936 mmol), 1H-pyrazolyl-4-N-methylformamide (0.30 g, 2.38727 mmol), copper(I) bromide-dimethyl sulfide (25 mg, 0.11936 mmol), triphenyl phosphine (31 mg, 0.11936 mmol), tripotassium phosphate (0.304 g, 1.4323 mmol) and sodium hydroxide (53 mg, 1.3130 mmol) are added, with 10 mL of anhydrous methylbenzene as solvent. The resulting mixture is heated to 50 Celsius degrees and stirred overnight under argon. After the reaction is completed as determined by thin layer chromatography, the reaction mixture is cooled to 20±5 Celsius degrees, water (30 ml) and ethyl acetate (35 ml) are then added thereto. The resulting mixture is shortly stirred and separated, with the organic phase washed by salt solution (25 ml), dried by magnesium sulphate, filtered, and with the resulting organic phase dried by suction to obtain an oily substance. The oily substance is separated and purified by silica gel column chromatography (mobile phase: hexane:ethyl acetate=3:1 to 2:1) to obtain 45 mg of light yellow powdery material, identified as 1-{1-[(4-cyano-3-trifluoromethyl-phenyl)-amino]-2-methyl-1-oxopropyl-2-yl}-N-methyl-1H-pyrazolyl-4-formamide, with a yield of 10%.

Nuclear magnetic resonance spectrum: $^1$H NMR (400 MHz, DMSO-$d_6$) δ10.03 (s, 1H, NH), 8.52-8.48 (m, 2H, NH+ pyrazolyl-H), 8.25 (d, J=1.2 Hz, 1H, ArH), 8.15 (dd, J=8.0 Hz, J=1.2 Hz, 1H, ArH), 8.09 (d, J=8.0 Hz, 1H, ArH), 8.02 (s, 1H, pyrazolyl-H), 1.82 (s, 6H, 2×CH$_3$), 1.37 (s, 3H, CH$_3$).

Mass spectrum: (ESI, Negative): 378.31[M−H]$^-$.

Example 22

Preparation of N-(6-cyano-5-trifluoromethyl-pyridyl-3-yl)-2-(4-fluoro-1H-pyrazolyl-1-yl-2-methylpropanamide

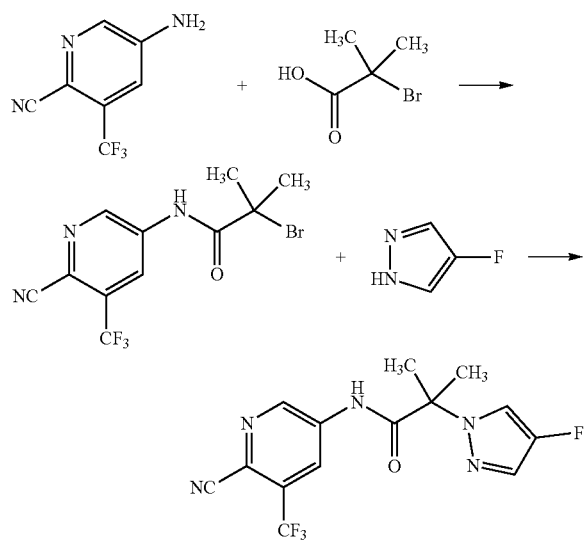

First Step of Reaction

Thionyl chloride (2.62 ml, 35.93 mmol) is added dropwise to a solution of 2-bromo-2-methyl propionic acid (5.00 g, 29.94 mmol) in 30 ml of anhydrous tetrahydrofuran at a temperature ranging from 0 to 12 Celsius degrees in 10 minutes. The resulting mixture is stirred under the same conditions for 2 hours. The internal temperature is adjusted to about −5 Celsius degrees. Triethylamine ($Et_3N$) (5.42 ml, 38.92 mmol) is slowly added to the reaction mixture, with an internal temperature lower than 12 Celsius degrees. The resulting mixture is stirred under the same reaction conditions for 20 minutes, and a solution of 5-amino-3-trifluoromethyl-2-cyanopyridine (5.60 g, 29.94 mmol) in 20 mL of anhydrous tetrahydrofuran is then added dropwise thereto, and the resulting mixture is stirred at 50 Celsius degrees for two hours. After the reaction is completed as determined by thin layer chromatography, the reaction mixture is cooled to 20±5 Celsius degrees, water (50 ml) and ethyl acetate (50 ml) are then added thereto. The resulting mixture is shortly stirred and separated, with the organic phase washed by salt solution (30 ml), dried by magnesium sulphate, filtered, and with the resulting organic phase dried by suction to obtain an oily substance. The oily substance is separated and purified by silica gel column chromatography (mobile phase: dichloromethane:ethyl acetate=9:1) to obtain 8.0 g of 2-bromo-N-(6-cyano-5-trifluoromethyl-pyridyl-3-yl)-2-methylpropanamide, with a yield of 80% and a purity of 99% by HPLC (mobile phase: water and acetonitrile) (254 nm).

Nuclear magnetic resonance spectrum: $^1H$ NMR (400 MHz, DMSO-$d_6$) δ 10.73 (s, 1H, NH), 9.39 (d, J=2.0 Hz, 1H, ArH), 8.81 (d, J=2.0 Hz, 1H, ArH), 2.03 (s, 6H, 2×$CH_3$).

Mass spectrum: (ESI, Positive): 335.9951 [M+H]$^+$.

Second Step of Reaction

In a 100 mL round bottom flask, 2-bromo-N-(6-cyano-5-trifluoromethyl-pyridyl-3-yl)-2-methylpropanamide (0.30 g, 0.8926 mmol), 4-fluoro-1H-pyrazol (0.154 g, 1.7852 mmol), copper(I) bromide-dimethyl sulfide (18.3 mg, 0.08926 mmol), triphenyl phosphine (23.4 mg, 0.08926 mmol), tripotassium phosphate (0.227 g, 1.0711 mmol), and sodium hydroxide (39.3 mg, 0.9818 mmol) are added, with 10 mL of anhydrous methylbenzene as solvent. The resulting mixture is heated to 50 Celsius degrees and stirred under argon for 15 hours. After the reaction is completed as determined by thin layer chromatography, the reaction mixture is cooled to 20±5 Celsius degrees, water (30 ml) and ethyl acetate (35 ml) are then added thereto. The resulting mixture is shortly stirred and separated, with the organic phase washed by salt solution (25 ml), dried by magnesium sulphate, filtered, and with the resulting organic phase dried by suction to obtain an oily substance. The oily substance is separated and purified by silica gel column chromatography (mobile phase: dichloromethane:ethyl acetate=9:1) to obtain 0.11 g of light yellow powdery material, identified as N-(6-cyano-5-trifluoromethyl-pyridyl-3-yl)-2-(4-fluoro-1H-pyrazolyl-1-yl-2-methylpropanamide, with a yield of 36%.

Nuclear magnetic resonance spectrum: $^1H$ NMR (400 MHz, DMSO-$d_6$) δ10.29 (s, 1H, NH), 9.12 (d, J=2.0 Hz, 1H, ArH), 8.47 (d, J=2.0 Hz, 1H, ArH), 8.15 (d, J=4.8 Hz, 1H, pyrazolyl-H), 7.56 (d, J=4.0 Hz, 1H, pyrazolyl-H), 1.79 (s, 6H, 2×$CH_3$).

Mass spectrum: (ESI, Negative): 340.19[M−H]$^-$.

Example 23

Preparation of N-(4-cyano-3-trifluoromethyl)-phenyl-1-(4-fluoro-1H-pyrazolyl-1-yl)-cyclobutane-formamide

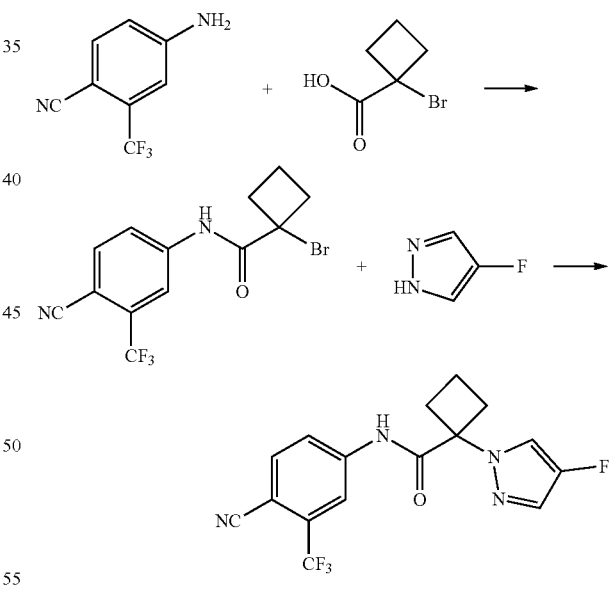

First Step of Reaction

Thionyl chloride (2.45 ml, 33.52 mmol) is added dropwise to a solution of 1-bromo-cyclobutane-formic acid (5.00 g, 27.93 mmol) in 30 ml of anhydrous tetrahydrofuran at a temperature ranging from 0 to 12 Celsius degrees in 10 minutes. The resulting mixture is stirred under the same conditions for 2 hours. The internal temperature is adjusted to about −5 Celsius degrees. Triethylamine ($Et_3N$) (5.06 ml, 36.31 mmol) is slowly added to the reaction mixture, with an internal temperature lower than 12 Celsius degrees. The resulting mixture is stirred under the same reaction conditions for 20 minutes, and a solution of 4-cyano-3-trifluoromethyl-phenylamine (5.20 g, 27.93 mmol) in 20 mL of anhydrous tetrahydrofuran is then added dropwise thereto, and the resulting mixture is stirred at 50 Celsius degrees for three hours. After the reaction is completed as determined by thin layer chromatography, the reaction mixture is cooled to 20±5 Celsius degrees, water (50 ml) and ethyl acetate (50 ml) are then added thereto. The resulting mixture is shortly stirred and separated, with the organic phase washed by salt solution (30 ml), dried by magnesium sulphate, filtered, and with the resulting organic phase dried by suction to obtain an oily substance. The oily substance is separated and purified by silica gel column chromatography (mobile phase: hexane:ethyl acetate=2:1) to obtain 7.95 g of yellow powdery material, identified as 1-bromo-N-(4-cyano-3-trifluoromethyl-phenyl)-cyclobutane-formamide, with a yield of 82% and a purity of 98.5% by HPLC (mobile phase: water and acetonitrile) (254 nm).

Nuclear magnetic resonance spectrum: $^1$H NMR (400 MHz, DMSO-$d_6$) δ 10.5 (s, 1H, NH), 8.36 (d, J=1.6 Hz, 1H, ArH), 8.23 (dd, J=8.4 Hz, J=1.6 Hz, 1H, ArH), 8.13 (d, J=8.4 Hz, 1H, ArH), 2.90-2.86 (m, 2H), 2.65-2.60 (m, 2H), 2.03-1.92 (m, 2H).

Mass spectrum: (ESI, Positive): 347.0002 [M+H]$^+$.

Second Step of Reaction

In a 100 mL round bottom flask, 1-bromo-N-(4-cyano-3-trifluoromethyl-phenyl)-cyclobutane-formamide (0.30 g, 0.8642 mmol), 4-fluoro-1H-pyrazol (0.149 g, 1.7285 mmol), copper(I) bromide-dimethyl sulfide (17.8 mg, 0.08642 mmol), triphenyl phosphine (22.7 mg, 0.08642 mmol), tripotassium phosphate (0.22 g, 1.0366 mmol), and sodium hydroxide (38 mg, 0.9507 mmol) are added, with 10 mL of anhydrous methylbenzene as solvent. The resulting mixture is heated to 50 Celsius degrees and stirred under argon for 15 hours. After the reaction is completed as determined by thin layer chromatography, the reaction mixture is cooled to 20±5 Celsius degrees, water (30 ml) and ethyl acetate (35 ml) are then added thereto. The resulting mixture is shortly stirred and separated, with the organic phase washed by salt solution (25 ml), dried by magnesium sulphate, filtered, and with the resulting organic phase dried by suction to obtain an oily substance. The oily substance is separated and purified by silica gel column chromatography (mobile phase: hexane:ethyl acetate=2:1) to obtain 0.106 g of light yellow powdery material, identified as N-(4-cyano-3-trifluoromethyl)-phenyl-1-(4-fluoro-1H-pyrazolyl-1-yl)-cyclobutane-formamide, with a yield of 35%.

Nuclear magnetic resonance spectrum: $^1$H NMR (400 MHz, DMSO-$d_6$) 510.02 (s, 1H, NH), 8.26 (d, J=2.0 Hz, 1H, ArH), 8.15-8.15 (m, 2H, ArH+pyrazolyl-H), 8.11 (d, J=8.4 Hz, 1H, ArH), 7.55 (d, J=4.0 Hz, 1H, pyrazolyl-H), 2.89-2.85 (m, 2H), 2.65-2.59 (m, 2H), 2.02-1.91 (m, 2H), 1.78 (s, 6H, 2×CH$_3$).

Mass spectrum: (ESI, Negative): 351.19[M–H]$^-$.

Example 24

Preparation of N-(6-cyano-5-trifluoromethyl-pyridyl-3-yl)-1-(4-fluoro-1H-pyrazolyl-1-yl)-cyclobutane-formamide

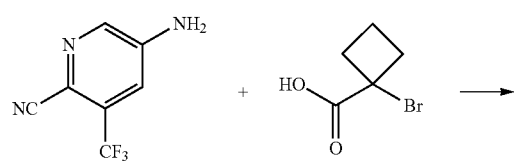

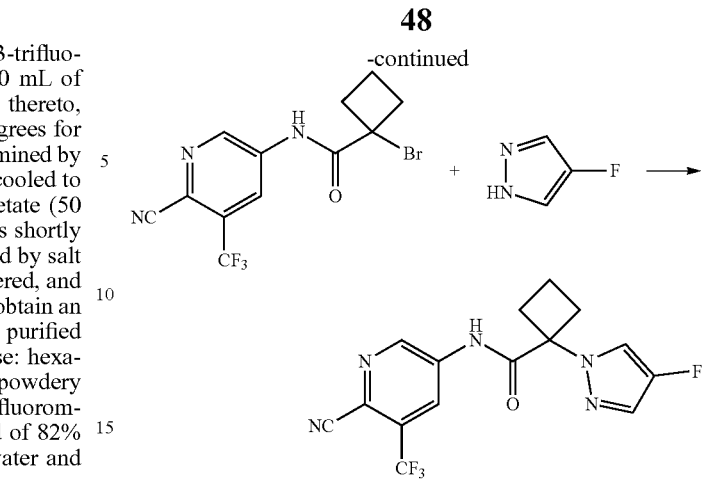

First Step of Reaction

Thionyl chloride (2.45 ml, 33.52 mmol) is added dropwise to a solution of 1-bromo-cyclobutane-formic acid (5.00 g, 27.93 mmol) in 30 ml of anhydrous tetrahydrofuran at a temperature ranging from 0 to 12 Celsius degrees in 10 minutes. The resulting mixture is stirred under the same conditions for 2 hours. The internal temperature is adjusted to about −5 Celsius degrees. Triethylamine (Et$_3$N) (5.06 ml, 36.31 mmol) is slowly added to the reaction mixture, with an internal temperature lower than 12 Celsius degrees. The resulting mixture is stirred under the same reaction conditions for 20 minutes, and a solution of 5-amino-3-trifluoromethyl-2-cyanopyridine (5.23 g, 27.93 mmol) in 20 mL of anhydrous tetrahydrofuran is then added dropwise thereto, and the resulting mixture is stirred at 50 Celsius degrees for three hours. After the reaction is completed as determined by thin layer chromatography, the reaction mixture is cooled to 20±5 Celsius degrees, water (50 ml) and ethyl acetate (50 ml) are then added thereto. The resulting mixture is shortly stirred and separated, with the organic phase washed by salt solution (30 ml), dried by magnesium sulphate, filtered, and with the resulting organic phase dried by suction to obtain an oily substance. The oily substance is separated and purified by silica gel column chromatography (mobile phase: dichloromethane:ethyl acetate=9:1) to obtain 7.70 g of yellow powdery material, identified as 1-bromo-N-(6-cyano-5-trifluoromethyl-pyridyl-3-yl)-cyclobutane-formamide, with a yield of 75% and a purity of 98.5% by HPLC (mobile phase: water and acetonitrile) (254 nm).

Nuclear magnetic resonance spectrum: $^1$H NMR (400 MHz, DMSO-$d_6$) δ 10.77 (s, 1H, NH), 9.40 (d, J=2.0 Hz, 1H, ArH), 8.85 (d, J=2.0 Hz, 1H, ArH), 2.82-2.78 (m, 2H), 2.59-2.53 (m, 2H), 2.04-1.95 (m, 2H).

Mass spectrum: (ESI, Positive): 347.09951 [M+H]$^+$.

Second Step of Reaction

In a 100 mL round bottom flask, 1-bromo-N-(6-cyano-5-trifluoromethyl-pyridyl-3-yl)-2-cyclobutane-formamide (0.30 g, 0.8618 mmol), 4-fluoro-1H-pyrazol (0.148 g, 1.7236 mmol), copper(I) bromide-dimethyl sulfide (17.7 mg, 0.08618 mmol), triphenyl phosphine (22.6 mg, 0.08618 mmol), tripotassium phosphate (0.22 g, 1.0341 mmol), and sodium hydroxide (38 mg, 0.9480 mmol) are added, with 10 mL of anhydrous methylbenzene as solvent. The resulting mixture is heated to 50 Celsius degrees and stirred under argon for 15 hours. After the reaction is completed as determined by thin layer chromatography, the reaction mixture is cooled to 20±5 Celsius degrees, water (30 ml) and ethyl acetate (35 ml) are then added thereto. The resulting mixture is shortly stirred and separated, with the organic phase washed by salt solution (25 ml), dried by magnesium sulphate, filtered, and with the resulting organic phase dried by suction to obtain an oily substance. The oily substance is separated and purified by silica gel column chromatography (mobile phase: dichloromethane:ethyl acetate=9:1) to obtain 82 mg of yellow powdery material, identified as N-(6-cyano-5-trifluoromethyl-pyridyl-3-yl)-1-(4-fluoro-1H-pyrazolyl-1-yl)-cyclobutane-formamide, with a yield of 27%.

Nuclear magnetic resonance spectrum: $^1$H NMR (400 MHz, DMSO-d$_6$) δ 10.25 (s, 1H, NH), 9.10 (d, J=2.0 Hz, 1H, ArH), 8.72 (d, J=2.0 Hz, 1H, ArH), 8.13 (d, J=4.8 Hz, 1H, pyrazolyl-H), 7.51 (d, J=4.0 Hz, 1H, pyrazolyl-H), 2.91-2.86 (m, 2H), 2.67-2.60 (m, 2H), 2.05-1.93 (m, 2H), 1.89 (s, 6H, 2×CH$_3$).

Mass spectrum: (ESI, Negative): 352.21[M−H]$^-$.

Example 25

Preparation of 2-(4-bromo-3-fluoro-1H-pyrazolyl-1-yl)-N-(4-cyano-3-trifluoromethyl)-phenyl-2-methyl-propanamide

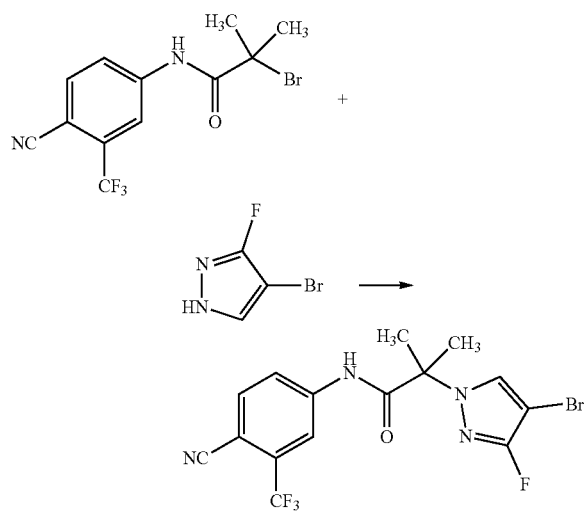

In a 100 mL round bottom flask, 2-bromo-N-(4-cyano-3-trifluoromethyl-phenyl)-2-methylpropanamide (0.40 g, 1.1936 mmol), 4-bromo-3-fluoro-1H-pyrazol (0.394 g, 2.38727 mmol), copper(I) bromide-dimethyl sulfide (25 mg, 0.11936 mmol), triphenyl phosphine (31 mg, 0.11936 mmol), tripotassium phosphate (0.304 g, 1.4323 mmol), and sodium hydroxide (53 mg, 1.3130 mmol) are added, with 10 mL of anhydrous methylbenzene as solvent. The resulting mixture is heated to 50 Celsius degrees and stirred under argon for 14 hours. After the reaction is completed as determined by thin layer chromatography, the reaction mixture is cooled to 20±5 Celsius degrees, water (30 ml) and ethyl acetate (35 ml) are then added thereto. The resulting mixture is shortly stirred and separated, with the organic phase washed by salt solution (25 ml), dried by magnesium sulphate, filtered, and with the resulting organic phase dried by suction to obtain an oily substance. The oily substance is separated and purified by silica gel column chromatography (mobile phase: hexane:ethyl acetate=3:1 to 2:1) to obtain 0.24 g of almost white powdery material, identified as 2-(4-bromo-3-fluoro-1H-pyrazolyl-1-yl)-N-(4-cyano-3-trifluoromethyl)-phenyl-2-methylpropanamide, with a yield of 48%.

Nuclear magnetic resonance spectrum: $^1$H NMR (400 MHz, DMSO-d$_6$) δ 10.04 (s, 1H, NH), 8.25 (d, J=2.0 Hz, 1H, ArH), 8.16-8.14 (m, 2H, ArH+pyrazolyl-H), 8.10 (d, J=8.4 Hz, 1H, ArH), 1.84 (s, 6H, 2×CH$_3$).

Mass spectrum: (ESI, Negative): 417.02 [M−H]$^-$.

Example 26

Preparation of 2-(3,4-difluoro-1H-pyrazolyl-1-yl)-N-(4-cyano-3-trifluoromethyl)-phenyl-2-methylpropanamide

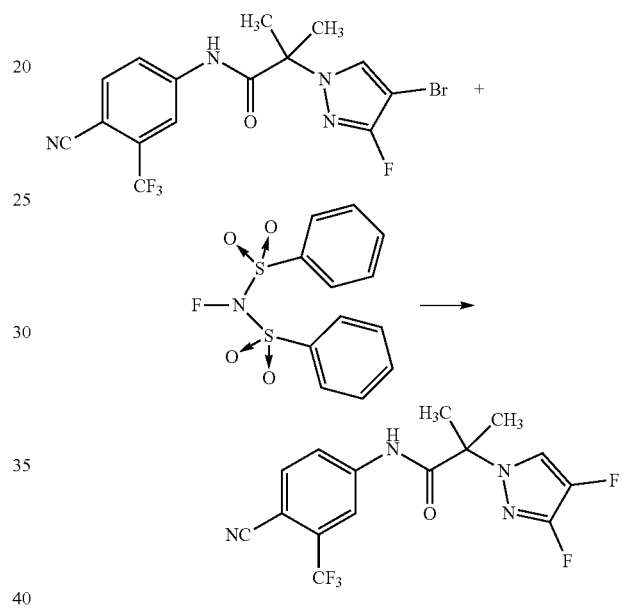

In a 100 mL round bottom flask, 2-(4-bromo-3-fluoro-1H-pyrazolyl-1-yl)-N-(4-cyano-3-trifluoromethyl) phenyl-2-methylpropanamide (0.20 g, 0.4771 mmol) is added, with 4 mL of anhydrous tetrahydrofuran as solvent. The resulting mixture is stirred under argon for 5 minutes, and then cooled to −78 Celsius degrees with a dry ice-acetone bath. A solution of 2.5 mol of N-butyllithium (0.382 ml, 0.9542 mmol) is added to the above reaction mixture, and the resulting mixture is stirred under the same conditions for 15 minutes. A solution of N-fluorobenzenesulfonimide (0.15 g, 0.4771 mmol) in 2.0 ml of anhydrous tetrahydrofuran is then added to the above reaction mixture. The resulting reaction mixture is gradually returned to room temperature and stirred under argon for 15 hours. After the reaction is completed as determined by thin layer chromatography, salt solution (20 ml) and ethyl acetate (30 ml) are then added thereto. The resulting mixture is shortly stirred and separated, with the organic phase washed by salt solution (25 ml), dried by magnesium sulphate, filtered, and with the resulting organic phase dried by suction to obtain an oily substance. The oily substance is separated and purified by silica gel column chromatography (mobile phase: dichloromethane:ethyl acetate=9:1) to obtain 43 mg of light yellow powdery material, identified as 2-(3,4-difluoro-1H-pyrazolyl-1-yl)-N-(4-cyano-3-trifluoromethyl)-phenyl-2-methylpropanamide, with a yield of 25%.

Nuclear magnetic resonance spectrum: $^1$H NMR (400 MHz, DMSO-d$_6$) δ 10.36 (s, 1H, NH), 8.43 (d, J=2.0 Hz, 1H, ArH), 8.22 (dd, J=8.0 Hz, J=2.0 Hz, 1H, ArH), 8.10 (d, J=8.0 Hz, 1H, ArH), 7.85 (m, 1H, pyrazolyl-H), 1.90 (s, 6H, 2×CH$_3$).

Mass spectrum: (ESI, Negative): 357.16 [M−H]$^-$.

Example 27

Preparation of 2-(3-chloro-4-methyl-1H-pyrazolyl-1-yl)-N-(4-cyano-3-trifluoromethyl)-phenyl-2-methylpropanamide

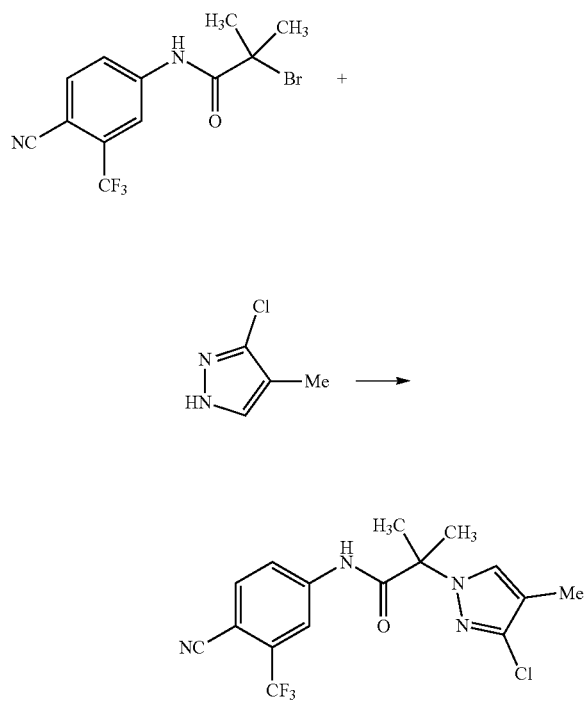

In a 100 mL round bottom flask, 2-bromo-N-(4-cyano-3-trifluoromethyl-phenyl)-2-methylpropanamide (0.40 g, 1.1936 mmol), 3-chloro-4-methyl-1H-pyrazol (0.278 g, 2.38727 mmol), copper(I) bromide-dimethyl sulfide (25 mg, 0.11936 mmol), triphenyl phosphine (31 mg, 0.11936 mmol), tripotassium phosphate (0.304 g, 1.4323 mmol), and sodium hydroxide (53 mg, 1.3130 mmol) are added, with 10 mL of anhydrous methylbenzene as solvent. The resulting mixture is heated to 50 Celsius degrees and stirred under argon for 14 hours. After the reaction is completed as determined by thin layer chromatography, the reaction mixture is cooled to 20±5 Celsius degrees, water (30 ml) and ethyl acetate (35 ml) are then added thereto. The resulting mixture is shortly stirred and separated, with the organic phase washed by salt solution (25 ml), dried by magnesium sulphate, filtered, and with the resulting organic phase dried by suction to obtain an oily substance. The oily substance is separated and purified by silica gel column chromatography (mobile phase: hexane:ethyl acetate=3:1 to 2:1) to obtain 0.16 g of almost white powdery material, identified as 2-(3-chloro-4-methyl-1H-pyrazolyl-1-yl)-N-(4-cyano-3-trifluoromethyl)-phenyl-2-methylpropanamide, with a yield of 36.4%.

Nuclear magnetic resonance spectrum: $^1$H NMR (400 MHz, DMSO-d$_6$) δ 10.00 (s, 1H, NH), 8.22 (d, J=1.0 Hz, 1H, ArH), 8.13 (dd, J=8.4 Hz, 1H, ArH), 8.10 (d, J=8.4 Hz, 1H, ArH), 7.91 (s, 1H, pyrazolyl-H), 1.91 (s, 3H, CH$_3$), 1.82 (s, 6H, 2×CH$_3$).

Mass spectrum: (ESI, Negative): 369.12 [M−H]$^-$.

Example 28

Preparation of 2-(3-bromo-4-chloro-1H-pyrazolyl-1-yl)-N-(4-cyano-3-trifluoromethyl)-phenyl-2-methylpropanamide

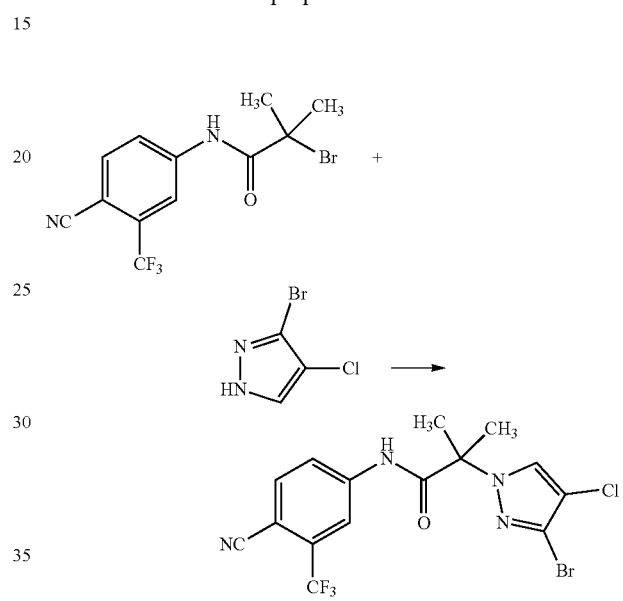

In a 100 mL round bottom flask, 2-bromo-N-(4-cyano-3-trifluoromethyl-phenyl)-2-methylpropanamide (0.40 g, 1.1936 mmol), 3-bromo-3-chloro-1H-pyrazol (0.433 g, 2.38727 mmol), copper(I) bromide-dimethyl sulfide (25 mg, 0.11936 mmol), triphenyl phosphine (31 mg, 0.11936 mmol), tripotassium phosphate (0.304 g, 1.4323 mmol), and sodium hydroxide (53 mg, 1.3130 mmol) are added, with 10 mL of anhydrous methylbenzene as solvent. The resulting mixture is heated to 50 Celsius degrees and stirred under argon for 14 hours. After the reaction is completed as determined by thin layer chromatography, the reaction mixture is cooled to 20±5 Celsius degrees, water (30 ml) and ethyl acetate (35 ml) are then added thereto. The resulting mixture is shortly stirred and separated, with the organic phase washed by salt solution (25 ml), dried by magnesium sulphate, filtered, and with the resulting organic phase dried by suction to obtain an oily substance. The oily substance is separated and purified by silica gel column chromatography (mobile phase: hexane:ethyl acetate=3:1 to 2:1) to obtain 0.22 g of white powdery material, identified as 2-(3-bromo-4-chloro-1H-pyrazolyl-1-yl)-N-(4-cyano-3-trifluoromethyl)-phenyl-2-methylpropanamide, with a yield of 42.3%.

Nuclear magnetic resonance spectrum: $^1$H NMR (400 MHz, DMSO-d$_6$) δ 10.01 (s, 1H, NH), 8.24-8.21 (m, 2H, ArH+pyrazolyl-H), 8.13 (d, J=8.8 Hz, 1H, ArH), 8.10 (d, J=8.8 Hz, 1H, ArH), 1.81 (s, 6H, 2×CH$_3$).

Mass spectrum: (ESI, Negative): 433.01 [M−H]$^-$.

Example 29

Preparation of 2-(3-fluoro-4-chloro-1H-pyrazolyl-1-yl)-N-(4-cyano-3-trifluoromethyl)-phenyl-2-methyl-propanamide

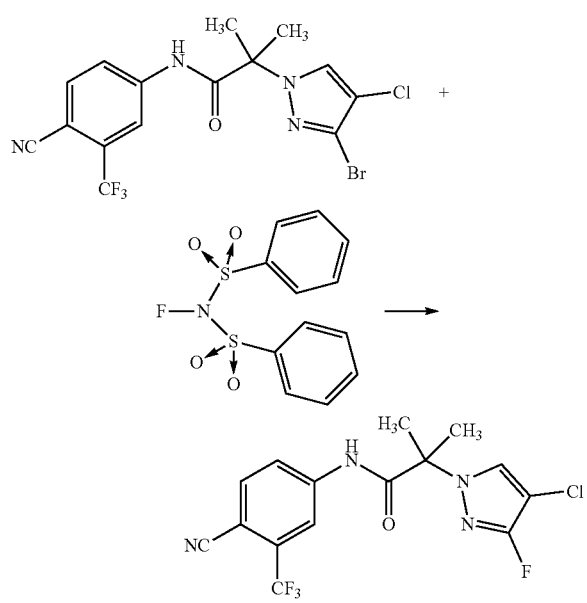

In a 100 mL round bottom flask, 2-(3-bromo-4-chloro-1H-pyrazolyl-1-yl)-N-(4-cyano-3-trifluoromethyl) phenyl-2-methylpropanamide (0.20 g, 0.4591 mmol) is added, with 4 mL of anhydrous tetrahydrofuran as solvent. The resulting mixture is stirred under argon for 5 minutes, and then cooled to −78 Celsius degrees with a dry ice-acetone bath. A solution of 2.5 mol of N-butyllithium (0.367 ml, 0.9182 mmol) is added to the above reaction mixture, and the resulting mixture is stirred under the same conditions for 15 minutes. A solution of N-fluorobenzenesulfonimide (0.145 g, 0.4591 mmol) in 2.0 ml of anhydrous tetrahydrofuran is then added to the above reaction mixture. The resulting reaction mixture is gradually returned to room temperature and stirred under argon for 15 hours. After the reaction is completed as determined by thin layer chromatography, salt solution (20 ml) and ethyl acetate (30 ml) are then added thereto. The resulting mixture is shortly stirred and separated, with the organic phase washed by salt solution (25 ml), dried by magnesium sulphate, filtered, and with the resulting organic phase dried by suction to obtain an oily substance. The oily substance is separated and purified by silica gel column chromatography (mobile phase: dichloromethane:ethyl acetate=9:1) to obtain 50 mg of yellow powdery material, identified as 2-(3-fluoro-4-chloro-1H-pyrazolyl-1-yl)-N-(4-cyano-3-trifluoromethyl)-phenyl-2-methylpropanamide, with a yield of 29%.

Nuclear magnetic resonance spectrum: $^1$H NMR (400 MHz, DMSO-$d_6$) δ 10.35 (s, 1H, NH), 8.44 (d, J=1.6 Hz, 1H, ArH), 8.23 (dd, J=8.2 Hz, J=1.6 Hz, 1H, ArH), 8.11 (d, J=8.2 Hz, 1H, ArH), 7.97 (d, J=3.6 Hz, 1H, pyrazolyl-H), 1.89 (s, 6H, 2×CH$_3$).

Mass spectrum: (ESI, Negative): 373.10 [M−H]$^-$.

Example 30

Preparation of 2-(3-chloro-4-cyano-1H-pyrazolyl-1-yl)-N-(4-cyano-3-trifluoromethyl)-phenyl-2-methyl-propanamide

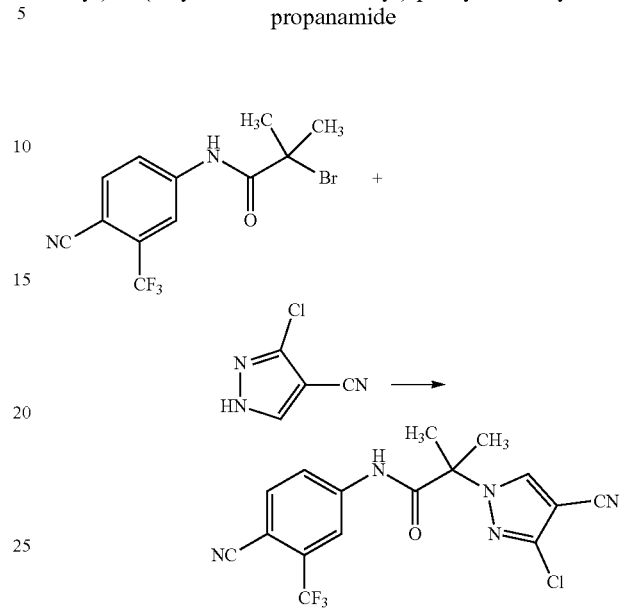

In a 100 mL round bottom flask, 2-bromo-N-(4-cyano-3-trifluoromethyl-phenyl)-2-methylpropanamide (0.40 g, 1.1936 mmol), 3-chloro-4-cyano-1H-pyrazol (0.304 g, 2.38727 mmol), copper(I) bromide-dimethyl sulfide (25 mg, 0.11936 mmol), triphenyl phosphine (31 mg, 0.11936 mmol), tripotassium phosphate (0.304 g, 1.4323 mmol), and sodium hydroxide (53 mg, 1.3130 mmol) are added, with 10 mL of anhydrous methylbenzene as solvent. The resulting mixture is heated to 50 Celsius degrees and stirred under argon for 14 hours. After the reaction is completed as determined by thin layer chromatography, the reaction mixture is cooled to 20±5 Celsius degrees, water (30 ml) and ethyl acetate (35 ml) are then added thereto. The resulting mixture is shortly stirred and separated, with the organic phase washed by salt solution (25 ml), dried by magnesium sulphate, filtered, and with the resulting organic phase dried by suction to obtain an oily substance. The oily substance is separated and purified by silica gel column chromatography (mobile phase: hexane:ethyl acetate=3:1 to 2:1) to obtain 0.16 g of white powdery material, identified as 2-(3-chloro-4-cyano-1H-pyrazolyl-1-yl)-N-(4-cyano-3-trifluoromethyl)-phenyl-2-methylpropanamide, with a yield of 35%.

Nuclear magnetic resonance spectrum: $^1$H NMR (400 MHz, DMSO-$d_6$) δ 9.99 (s, 1H, NH), 8.69 (s, 1H, pyrazolyl-H), 8.21 (s, 1H, ArH), 8.12 (d, J=8.4 Hz, H, ArH), 8.10 (d, J=8.4 Hz, 1H, ArH), 1.83 (s, 6H, 2×CH$_3$).

Mass spectrum: (ESI, Negative): 380.15 [M−H]$^-$.

II. EXAMPLES FOR PREPARING FORMULATIONS

Example A for Formulation: Preparation of an Injection (i). Formulation Composition:

| | |
|---|---|
| Compound of Example 15 | 25 g |
| Polysorbate 80 | 20 g |

-continued

| | |
|---|---|
| Mannitol | 10 g |
| Injection water to | 5000 ml |
| | 1000 pcs |

(ii). Preparation Method:

In accordance with the formulation composition, the compound of example 15, polysorbate 80 and mannitol are added to 4000 ml of injection water. The resulting mixture is stirred and dissolved, and thereafter injection water is then added until the total volume of the resulting mixture reaches 5000 ml. The resulting mixture is further stirred, and sterilized by filtration through microporous filter (0.22 μM), and the filtrate is aseptically filled in 5 ml of ampoules with 5 ml filtrate per ampoule (spec: 25 mg per ampoule), sealed and sterilized.

Example B for Formulation: Preparation of a Tablet (i). Formulation Composition:

Formulation 2-1 Formulation for Tablet with Formula I (Weight Per 1000 Tablets)

| | |
|---|---|
| Compound of Example 15 | 200 g |
| Lactose | 100 g |
| Microcrystalline cellulose | 60 g |
| Pregelatinized starch | 40 g |
| Carboxymethyl starch sodium | 40 g |
| Aerosil | 4 g |
| Magnesium stearate | 4 g |
| 0.3% HPMC | appropriate amount |
| | 1000 pieces |

Formulation 2-2 Formulation for Tablet with Formula I (Weight Per 1000 Tablets)

| | |
|---|---|
| Compound of Example 15 | 50 g |
| Lactose | 50 g |
| Microcrystalline cellulose | 15 g |
| Pregelatinized starch | 10 g |
| Carboxymethyl starch sodium | 10 g |
| Aerosil | 0.1 g |
| Magnesium stearate | 1 g |
| 0.3% HPMC | appropriate amount |
| | 1000 pieces |

Formulation 2-3 Formulation for Tablet with Formula I (Weight Per 1000 Tablets)

| | |
|---|---|
| Compound of Example 15 | 10 g |
| Lactose | 10 g |
| Microcrystalline cellulose | 3 g |
| Pregelatinized starch | 2 g |
| Carboxymethyl starch sodium | 2 g |
| Aerosil | 0.02 g |
| Magnesium stearate | 0.2 g |
| 0.3% HPMC | appropriate amount |
| | 1000 pieces |

(ii) Preparation Method:

The compound of Example 15, lactose and part of microcrystalline cellulose are micronize in a ratio of 200:100:40, and the remaining microcrystalline cellulose, pregelatinized starch, Aerosil and carboxymethyl starch sodium in accordance with the formulation which are sieved by 80 mesh are added therein and well mixed, and thereafter 0.3% HPMC solution is added therein to prepare soft material which is then granulated with 18 mesh. The resulting granule is dried at 60 Celsius degrees (controlling the moisture content of the granule at about 3%), and magnesium stearate sieved with 80 mesh is added and mixed with the granule. The resulting granule is sieved with 16 mesh, tableted and packaged.

III. BIOLOGICAL ACTIVITY DETECTION

Reagents and instruments: radiolabeled dihydrotestosterone (DHT-d3) and unlabeled dihydrotestosterone (DHT) purchased from Sigma-Aldrich (St. Louis, Mo.), scintillation solution purchased from Perkin Elmer Life Sciences (Boston, Mass.), hydroxyapatite (HAP) suspension purchased from Bio-Rad Laboratories (Hercules, Calif.), buffer (containing 10 mM Tris, 1.5 mM disodium EDTA, 0.25 M sucrose, 10 mM sodium molybdate and 1 mM PMSF, pH value adjusted to 7.4), and hydroxyapatite (HAP) solution (containing 50 mM Tris and 1 mM $KH_2PO_4$, pH value adjusted to 7.4).

In the present invention, the biological activity of the N-aromatic amide compounds with the formula (I) and/or (II) is measured accord to the following method. The compounds of the present invention obtained from the preparing examples and the control compounds are respectively dissolved in DMSO to prepare mother liquors with certain concentrations, which are diluted into several concentration gradients with DMSO, that are further diluted with buffer to have concentrations ranging from $10^{-1}$ nM to $10^4$ nM and stored in a refrigerator at 4 Celsius degrees for use. The androgen receptor (prepared from the prostate of male SD rats, 200-250 g of male Sprague-Dawley rats) and the radiolabeled dihydrotestosterone (DHT-d3, 84 Ci/mmol) are added to the buffer and well mixed for preparing reaction solution. The concentration gradients of the diluted compounds are respectively added into the reaction solution and well mixed, and the resulting mixtures are incubated at 4 Celsius degrees for 15 hours, so that the compounds and the dihydrotestosterone can fully react with the androgen receptor. Thereafter, the hydroxyapatite (HAP) suspension is added therein, well mixed, incubated for 10 minutes at 4 Celsius degrees, and centrifuged for removing the supernatant containing free dihydrotestosterone. The dihydrotestosterone bound to the androgen receptor is adsorbed in the hydroxyapatite and thus retained in the precipitated particles, thereby separating the bound and unbound radiolabelled ligands. A scintillation solution is added to the precipitate, well mixed, and detected for the radioactivity intensity using a WALLACE MicroBeta Trilux Scintillator (Perkin Elmer). The detected radioactivity intensity values for the concentration gradients are processed to obtain values of $IC_{50}$ and $K_i$. The specific biological activity (the competition results between androgen receptor ligand and radioligand) is shown in the following table:

| Compound | Structural Formula | Log P | IC$_{50}$ (μM) | K$_i$ (μM) |
|---|---|---|---|---|
| Bicalutamide (Control) | | 2.57 | 0.637 | 1.25 |
| (R) Bicalutamide (Control) | | 2.57 | 0.264 | 0.518 |
| Enzalutamide (Control) | | 4.56 | 0.218 | 2.75 |
| Compound of Example 1 | | 6.16 | 0.546 | |
| Compound of Example 2 | | 6.00 | 0.337 | |
| Compound of Example 3 | | 4.32 | 0.215 | 0.367 |

| Compound | Structural Formula | Log P | IC$_{50}$ (μM) | K$_i$ (μM) |
|---|---|---|---|---|
| Compound of Example 4 | | 4.32 | 0.246 | 0.491 |
| Compound of Example 5 | | 4.32 | 0.227 | 0.314 |
| Compound of Example 6 | | | 0.261 | 0.421 |
| Compound of Example 7 | | 4.72 | 0.253 | 0.295 |
| Compound of Example 8 | | 5.09 | 0.357 | 0.440 |
| Compound of Example 9 | | 4.20 | 0.232 | 0.445 |
| Compound of Example 10 | | 4.81 | 0.437 | 0.387 |

-continued
| Compound | Structural Formula | Log P | IC$_{50}$ (μM) | K$_i$ (μM) |
|---|---|---|---|---|
| Compound of Example 11 | 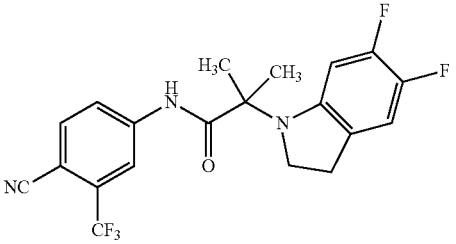 [SMILES: CC(C)(C(=O)Nc1ccc(C#N)c(C(F)(F)F)c1)N1CCc2cc(F)c(F)cc21] | 4.97 | 0.505 | 0.505 |
| Compound of Example 12 | 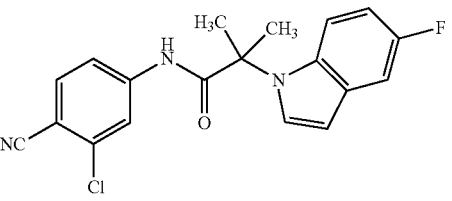 [SMILES: CC(C)(C(=O)Nc1ccc(C#N)c(Cl)c1)n1ccc2cc(F)ccc21] | 3.96 | 0.205 | 0.351 |
| Compound of Example 13 | 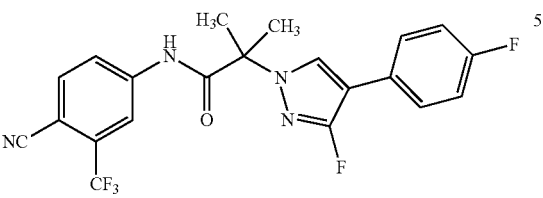 | 5.18 | 0.416 | |
| Compound of Example 14 | 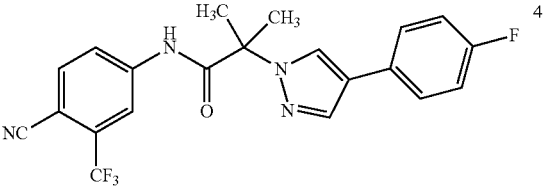 | 4.56 | 0.760 | |
| Compound of Example 15 | 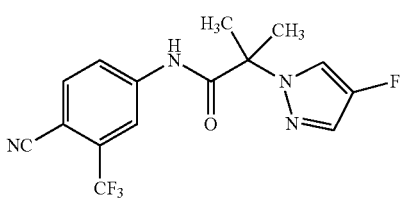 [SMILES: CC(C)(C(=O)Nc1ccc(C#N)c(C(F)(F)F)c1)n1cc(F)cn1] | 2.88 | 0.125 | |
| Compound of Example 16 | 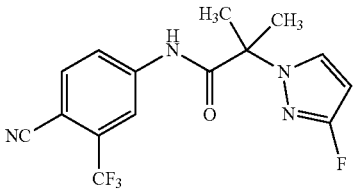 [SMILES: CC(C)(C(=O)Nc1ccc(C#N)c(C(F)(F)F)c1)n1ccc(F)n1] | 3.35 | 0.147 | |
| Compound of Example 17 | 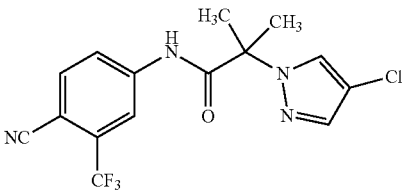 [SMILES: CC(C)(C(=O)Nc1ccc(C#N)c(C(F)(F)F)c1)n1cc(Cl)cn1] | 3.28 | 0.116 | |

-continued

| Compound | Structural Formula | Log P | IC$_{50}$ (μM) | K$_i$ (μM) |
|---|---|---|---|---|
| Compound of Example 18 | | 3.64 | 0.168 | |
| Compound of Example 19 | | | | |
| Compound of Example 20 | | 2.76 | 0.107 | |
| Compound of Example 21 | | 1.87 | | |
| Compound of Example 22 | | 1.97 | 0.073 | |
| Compound of Example 23 | | 2.94 | 0.115 | |
| Compound of Example 24 | | 2.02 | 0.068 | |

| Compound | Structural Formula | Log P | IC$_{50}$ (μM) | K$_i$ (μM) |
| --- | --- | --- | --- | --- |
| Compound of Example 25 | | 4.18 | 0.091 | |
| Compound of Example 26 | | 3.51 | 0.075 | |
| Compound of Example 27 | | 4.11 | 0.133 | |
| Compound of Example 28 | | 4.52 | 0.159 | |
| Compound of Example 29 | | 3.91 | 0.105 | |
| Compound of Example 30 | | 3.66 | 0.088 | |

Comparing the test compounds and the positive control groups, the following conclusions can be drawn:

Example 1 (IC$_{50}$=0.546 μM), Example 2 (IC$_{50}$=0.337 μM), Example 3 (IC$_{50}$=0.215 μM), Example 4 (IC$_{50}$=0.246 μM), Example 5 (IC$_{50}$=0.227 μM), Example 6 (IC$_{50}$=0.261 μM), Example 7 (IC$_{50}$=0.253 μM), Example 8 (IC$_{50}$=0.357 μM), Example 9 (IC$_{50}$=0.232 μM), Example 10 (IC$_{50}$=0.437 μM), Example 11 (IC$_{50}$=0.505 μM), Example 12 (IC$_{50}$=0.205 μM) and Example 13 (IC$_{50}$=0.416 μM) have significantly stronger antagonism to the androgen receptor than the bicalutumide (IC$_{50}$=0.637 μM) positive control groups.

Example 15 (IC$_{50}$=0.125 μM), Example 16 (IC$_{50}$=0.147 μM), Example 17 (IC$_{50}$=0.116 μM), Example 18 (IC$_{50}$=0.168 μM), Example 20 (IC$_{50}$=0.107 μM), Example 22 (IC$_{50}$=0.073 μM), Example 23 (IC$_{50}$=0.115 μM), Example 24 (IC$_{50}$=0.068 μM), Example 25 (IC$_{50}$=0.091 μM), Example 26 (IC$_{50}$=0.075 μM), Example 27 (IC$_{50}$=0.133 μM), Example 28 (IC$_{50}$=0.159 μM), Example 29 (IC$_{50}$=0.105 μM) and Example 30 (IC$_{50}$=0.088 μM) have significantly stronger antagonism to the androgen receptor than the latest generation of new anti-prostate cancer drug, enzalutamide (IC$_{50}$=0.215 μM) positive control group.

Example 3 (K$_i$=0.367 μM), Example 4 (IC$_{50}$=0.491 μM), Example 5 (K$_i$=0.314 μM), Example 6 (K$_i$=0.421 μM), Example 7 (K$_i$=0.295 μM), Example 8 (K$_i$=0.440 μM), Example 9 (K$_i$=0.445 μM), Example 10 (K$_i$=0.387 μM), Example 11 ($K_i$=0.505 μM) and Example 12 ($K_i$=0.351 μM) have stronger binding activity to the androgen receptor than bicalutumide control group ($K_i$=1.25 μM), and much stronger binding activity to the androgen receptor than enzalutamide control group ($K_i$=2.75 μM).

The detection results for the biological activity in the above table shows that, in comparison with the positive control groups (bicalutumide, and enzalamine), the compounds of the present invention are capable of binding more strongly to the androgen receptor and have stronger activity for anti-androgen receptor. Therefore, a new N-aromatic amide drug for anti-androgen which is safer and more effective than the existing drugs can be developed, and has an important value and status in the treatment of androgen-related diseases.

The compounds of the present invention can be used alone or as compositions for the prevention or treatment of various androgen-related diseases, such as prostate cancer, prostate hyperplasia, breast cancer, bladder cancer, and ovarian cancer, and also for the prevention or treatment of acne, hirsutism, psilosis and other diseases.

The above description is merely exemplary embodiments and examples of the present invention and is not intended to limit the scope of the invention, and any equivalent structure or equivalent process change made depending on the contents of this specification, or those directly or indirectly used in other related technical fields, fall in the scope of the present invention.

What is claimed is:

1. An N-aromatic amide compound of formula (IV) or a pharmaceutically acceptable salt or stereoisomer thereof:

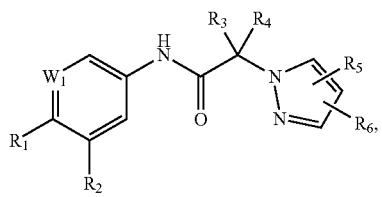

IV wherein each of $R_1$ and $R_2$ is cyano group, nitro group, or trifluoromethyl group;
each of $R_3$ and $R_4$ is $C_1$-$C_6$ alkyl group, or $R_3$ and $R_4$ together with carbon atom through which $R_3$ and $R_4$ are bound constitute a 3-6 membered cycloalkyl group;
each of $R_5$ and $R_6$ is hydrogen atom, halogen, trifluoromethyl group, cyano group, nitro group, acetyl group,

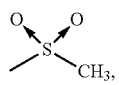

N-methylcarbamoyl group, $C_1$-$C_6$ alkyl group, aryl group or substituted aryl group;
$W_1$ is carbon atom or nitrogen atom; and
each of $R_5$ and $R_6$ is bound to any bondable site of the group

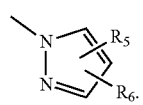

2. The N-aromatic amide compound or the pharmaceutically acceptable salt or stereoisomer thereof according to claim 1, wherein a stereoisomer of the compound is a racemic, levorotatory and/or dextrorotatory isomer.

3. The N-aromatic amide compound or the pharmaceutically acceptable salt or stereoisomer thereof according to claim 1, wherein the compound is selected from the group consisting of:

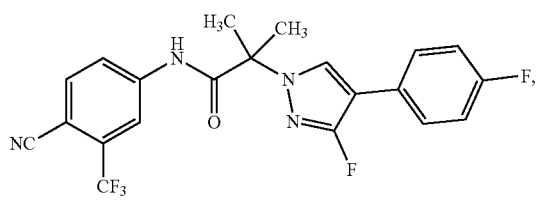

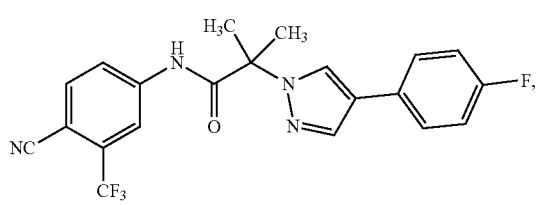

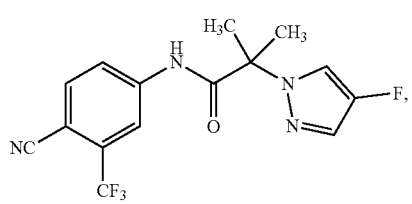

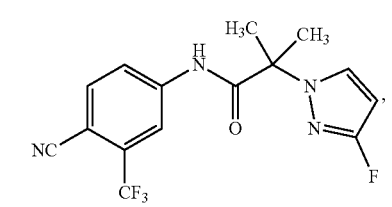

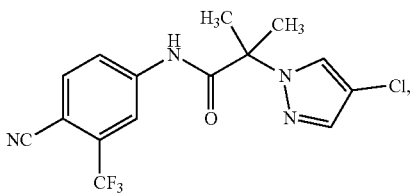

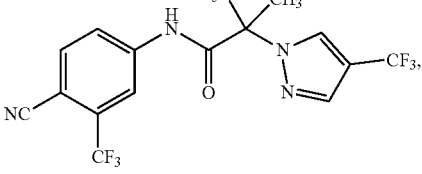

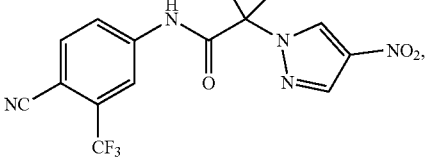

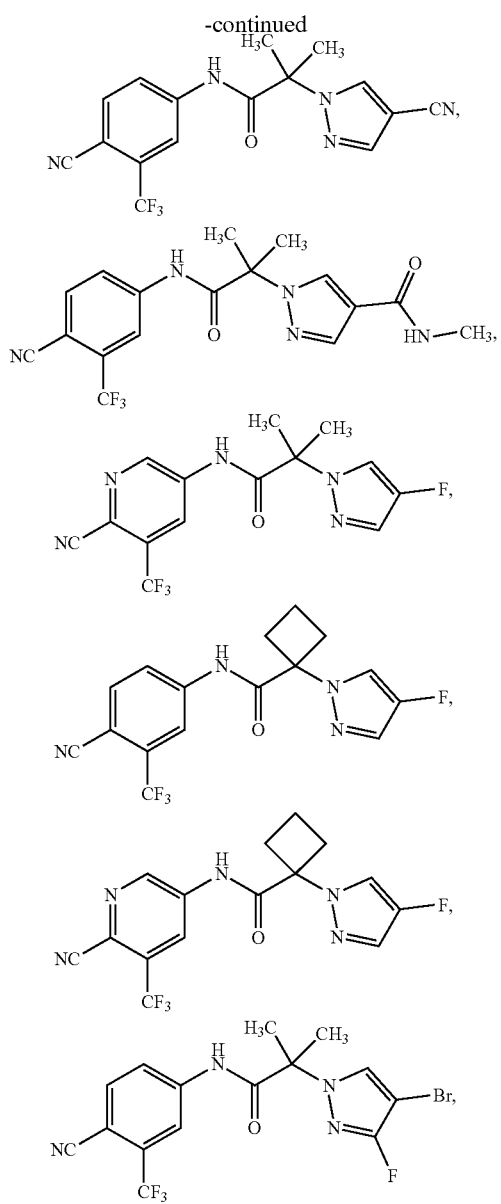
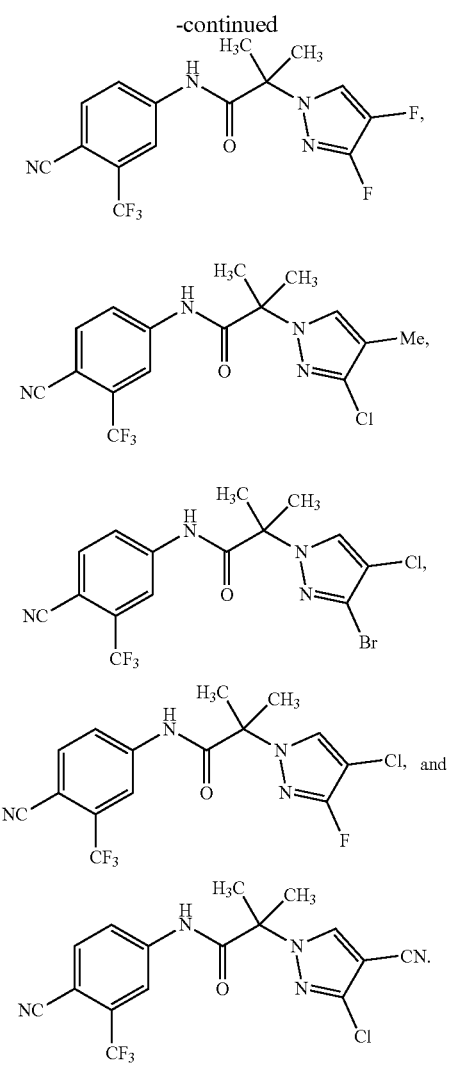
4. A pharmaceutical composition, comprising the N-aromatic amide compound or the pharmaceutically acceptable salt or stereoisomer thereof according to claim 1.
* * * * *